(12) United States Patent
Lee et al.

(10) Patent No.: US 8,552,208 B2
(45) Date of Patent: Oct. 8, 2013

(54) ANALOGS OF TETRAMIC ACID

(75) Inventors: Richard E. Lee, Cordova, TN (US); Julian Gregston Hurdle, Germantown, TN (US); Raghunandan Yendapally, Longmeadow, MA (US)

(73) Assignee: University of Tenneseee Research Foundation, Knoxville, TN (US)

( * ) Notice: Subject to any disclaimer, the term of this patent is extended or adjusted under 35 U.S.C. 154(b) by 608 days.

(21) Appl. No.: 12/231,915

(22) Filed: Sep. 8, 2008

(65) Prior Publication Data

US 2009/0069406 A1 Mar. 12, 2009

Related U.S. Application Data

(60) Provisional application No. 60/993,249, filed on Sep. 11, 2007.

(51) Int. Cl.
C07D 207/12 (2006.01)

(52) U.S. Cl.
USPC ......................................... 548/544

(58) Field of Classification Search
None
See application file for complete search history.

(56) References Cited

U.S. PATENT DOCUMENTS

| | | | |
|---|---|---|---|
| 3,306,909 A * | 2/1967 | Uloth | 548/537 |
| 5,420,155 A | 5/1995 | Kulagowski | |
| 5,874,589 A | 2/1999 | Campbell | |
| 6,387,943 B1 | 5/2002 | Ramakrishna | |
| 6,599,930 B2 | 7/2003 | Vertesy et al. | |
| 6,962,943 B2 | 11/2005 | Schiell | |
| 2005/0119329 A1 | 6/2005 | Godel | |
| 2007/0191336 A1 | 8/2007 | Flynn | |

FOREIGN PATENT DOCUMENTS

CN 1676515 A * 10/2005

OTHER PUBLICATIONS

La Croix et al. (Pesticide Science (1975), 6(5), pp. 491-496).*
Dixon DJ, et al, "Total synthesis of the polyenoyltetramic acid mycotoxin erythroskyrine," J. Chem. Soc., Perkin Trans., 1:839-841 (1999).
Ganzle MG, et al, "Characterization of reutericyclin produced by *Lactobacillus reuteri* LTH2584," Applied and Environmental Microbiology, 66(10):4325-4333 (2000).
Reusser, F, "Tirandimycin, an inhibitor of bacterial ribonucleic acid polymerase," Antimicrobial Agents and Chemotherapy, 10(4):618-622 (1976).

* cited by examiner

*Primary Examiner* — Alicia L Otton
(74) *Attorney, Agent, or Firm* — Howard Eisenberg, Esq.

(57) ABSTRACT

Tetramic acid analogues of Formula I and Formula II have antibacterial activity, primarily against gram-positive bacteria, and are iron chelators.

2 Claims, 8 Drawing Sheets

11l

11m

11n

11o

11p

A.

B.

13a

13b

13c

13d

13e

13f

13g

13h

13i

13j

13k

13l 13m          13n          13o

A.

B.

12a

12b

12c

12d

12e

12f

12g

12p

ANALOGS OF TETRAMIC ACID

This application claims the benefit of pending U.S. Provisional Patent Application Ser. No. 60/993,249, which was filed on Sep. 11, 2007.

This invention was developed in part by grants from the National Institutes of Health, grant no. 5P01AI057836-040001, and the U.S. government has certain rights in the invention.

FIELD OF THE INVENTION

This invention pertains to the field of chemical compounds that are effective in killing or reducing growth of bacteria, which compounds may be useful as in vitro or in vivo antibiotics.

BACKGROUND OF THE INVENTION

The ability to effectively treat bacterial infectious diseases through the use of antimicrobial chemotherapy has been severely affected by the widespread emergence of antibiotic resistance among bacterial pathogens. Examples of multi-drug resistant bacterial strains that have emerged include *Staphylococcus aureus, Streptococcus pyogenes, Streptococcus pneumoniae, Mycobacterium tuberculosis, Enterococcus faecalis, Proprionibacterium acnes,* and *Escherichia coli.* These antibiotic resistant bacteria present serious health care concerns worldwide and, in fact, antibiotic resistant bacteria are a major cause of morbidity and mortality in both hospital and community settings. There is therefore an urgent need to combat this problem effectively.

One approach to combating antibiotic resistance is to develop novel classes of compounds that exhibits good antibacterial activity and are applicable for the treatment and/or prophylactic management of bacterial infections. Naturally occurring tetramic acid derivatives are a great deal of interest because of their broad spectrum of antibacterial activity. Examples of naturally occurring tetramic acid derivates that exhibit antibacterial activity include reutericyclin, streptolydigin, PF1052, and erythroskyrine. No tetramic acid derivative antibiotics are marketed at present.

A significant need exists for tetramic acid derivatives having antibacterial activity which derivatives are can be produced synthetically.

DESCRIPTION OF THE INVENTION

Figure 1:
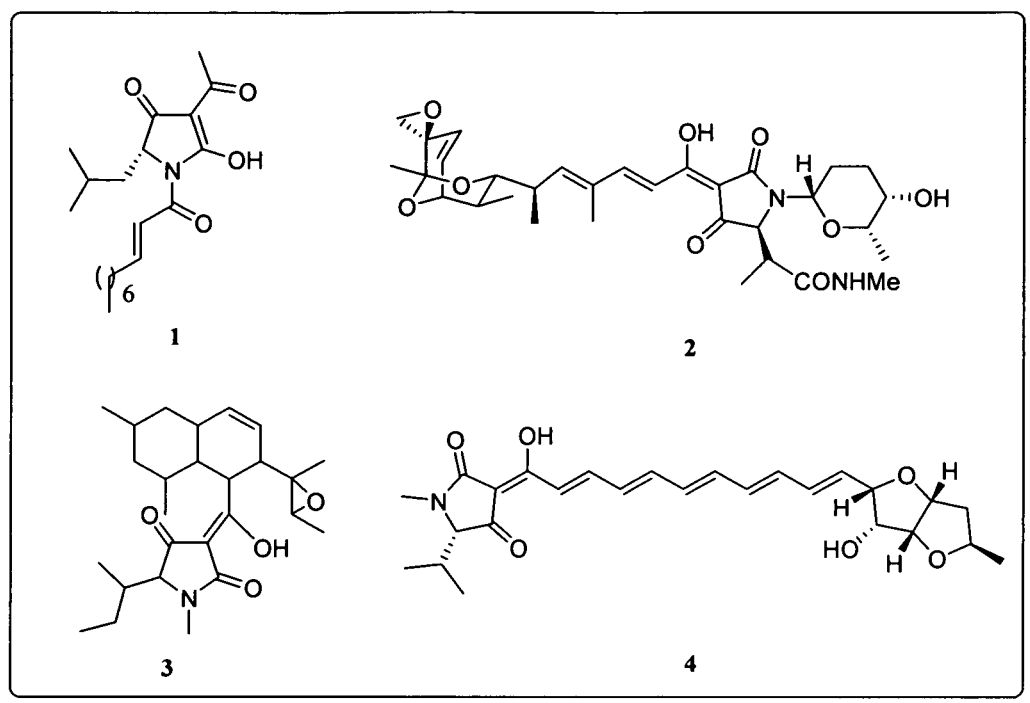
FIG. 1 shows the chemical structure of four naturally occurring tetramic acid derivatives having antibiotic activity. (1) is reutericyclin, (2) is streptolydigin, (3) is PF1052, and (4) is erythroskyrine.
Figure 2A:
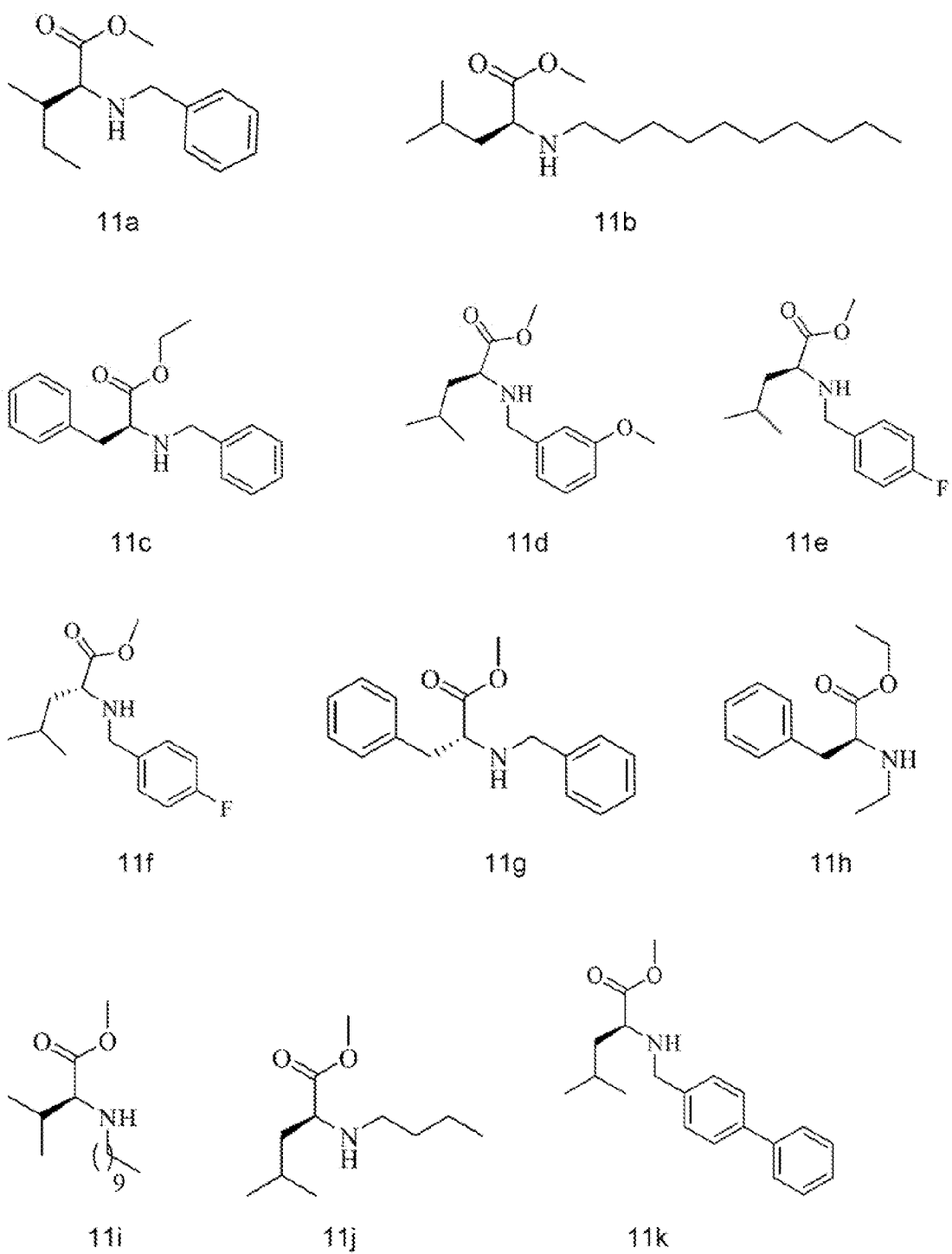
FIG. 2 shows the chemical structure of secondary amines used in the preparation of compounds of Formula I and Formula II of the invention. The secondary amines are designated 11a to 11p as follows. 11a is (2S,3S)-methyl 2-(benzylamino)-3-methylpentanoate. 11b is (S)-methyl 2-(decylamino)-4-methylpentanoate. 11c is (S)-ethyl 2-(benzylamino)-3-phenylpropanoate. 11d is (S)-methyl 2-(3-methoxybenzylamino)-4-methylpentanoate. 11e is (S)-methyl 2-(4-fluorobenzylamino)-4-methylpentanoate. 11f is (R)-methyl 2-(4-fluorobenzylamino)-4-methylpentanoate. 11g is (R)-methyl 2-(benzylamino)-3-phenylpropanoate. 11h is (S)-ethyl 2-(ethylamino)-3-phenylpropanoate. 11i is (S)-methyl 2-(decylamino)-3-methylbutanoate. 11j is (S)-methyl 2-(butylamino)-4-methylpentanoate. 11k is (S)-methyl 2-(biphenyl-4-ylmethylamino)-4-methylpentanoate. 11l is (2S)-methyl 2-((6,6-dimethylbicyclo[3.1.1]hept-2-en-2-yl)methylamino)-4-methylpentanoate. 11m is (2S)-methyl 2-(3,7-dimethyloct-6-enylamino)-4-methylpentanoate. 11n is (S)-ethyl 2-(decylamino)-3-phenylpropanoate. 11o is (R)-methyl 2-(decylamino)-4-methylpentanoate. 11p is (2S,3S)-methyl 2-(furan-2-ylmethylamino)-3-methylpentanoate.
Figure 2B:
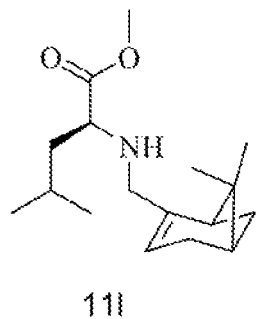
Figure 2B:
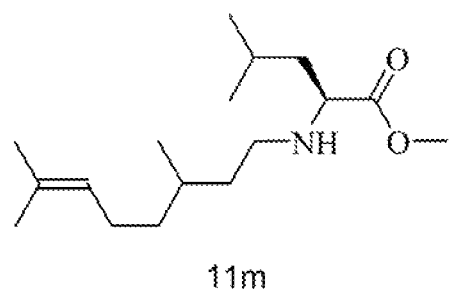
Figure 2B:
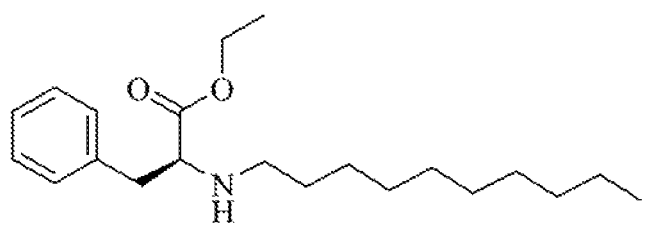
Figure 2B:
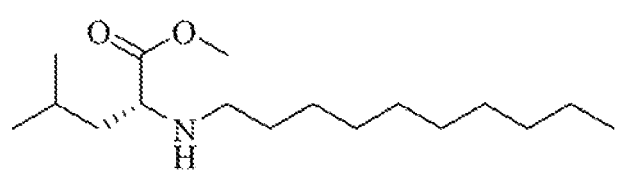
Figure 2B:
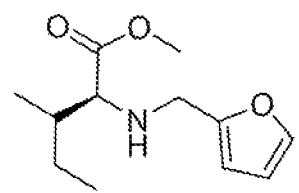

The inventors have discovered a series of tetramic acid analogs having antibacterial activity, which tetramic acid analogs are capable of being synthesized. The analogs are other than reutericyclin, streptolydigin, PF1052, and erythroskyrine. In contrast to reutericyclin, the analogs of the invention possess a more stable N-alkyl substitution rather than the N-amide substitution of reutericyclin. In contrast to streptolydigin, PF1052, and erythroskyrine, the analogs of the invention possess smaller more synthetically tractable acyl substitutions at the 3-position of the tetramic core and larger N-alkyl and N-aryl substitutions to the tetramic core.

In one embodiment, the present invention is a chemical compound that is an analog of tetramic acid. The chemical compound of the invention has antibacterial properties, particularly against gram positive bacteria.

In one embodiment, the chemical compound of the invention is an N-substituted, 3-acyl tetramic acid that has the formula shown below as Formula I in both major tautomeric forms:

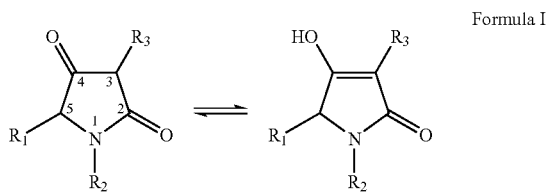

Formula I

A) wherein R1 is:
a) a straight alkyl chain of one to six carbons, such as methyl, ethyl, n-propyl, n-butyl, n-pentyl, or n-hexyl, or branched alkyl chain of one to six carbons,
b) a branched alkyl chain of three to six carbons, such as iso-propyl, iso-butyl, sec-butyl, tert-butyl, or iso-pentyl,
c) an alkyl ring system, such as cyclopropyl, cyclobutyl, cyclopentyl, cyclobutyl methyl, cyclopentyl methyl,
d) an aryl or aryl alkyl ring system, such as phenyl or benzyl, or substituted phenyl or benzyl, wherein examples of substituents are chloro, fluoro, bromo, hydroxyl, methyl, ethyl, methoxy, trifluoromethoxy, morpholinyl, and piperazinyl, or
e) a heteroaryl or heteroaryl alkyl ring system, such as imidazolyl, pyrrolyl, pyridinyl, pyrazinyl, indolyl, furanyl, thienyl, imidazolyl methyl, pyrrolyl methyl, pyridinyl methyl, pyrazinyl methyl, furanyl methyl, indolyl methyl and thienyl methyl, which ring system may or may not be substituted, which substituents may be for example, chloro, fluoro, bromo, hydroxyl, or methoxy.

B) wherein R2 is:
a) a straight alkyl side chain larger than 1 carbon, and preferably larger than 2 carbons,
b) a branched saturated alkyl system, such as iso-propyl, iso-butyl, sec-butyl, tert-butyl, or iso-pentyl,
c) a branched unsaturated alkyl chain of 3 to 16 carbons,
d) a saturated or unsaturated (monocyclic and bicyclic) ring systems of 3 to 16 carbons,
e) an aryl, biaryl, heteroaryl, or bihetero aryl ring system, such as benzyl, substituted benzyl, biphenyl, imidazolyl methyl, pyrrolyl methyl, pyridinyl methyl, pyrazinyl methyl, furanyl methyl, indolyl methyl, or thienyl methyl, wherein substituents may be, for example, chloro, fluoro, bromo, hydroxyl, or methoxy, and C) wherein R3 is an acyl moiety that may be:
a) from C2-C8 alkyl, such as acetyl, propionyl, butanoyl, etc.,
b) an aryl ring, such as benzoyl, which ring may be substituted, wherein examples of substituents may be chloro, fluoro, bromo, hydroxyl, methyl, ethyl, trifluoromethoxy, and methoxy, or
c) a heteroaryl or substituted heteroaryl ring system, containing groups such as furanoyl, imidazoyl, pyrrodyl, or indaloyl, which may contain substituents such as chloro, fluoro, bromo, hydroxyl, methyl, ethyl, and methoxy.

Preferably, R2 is not acyl, for example R2 is preferably not the acyl substitution present at the corresponding N position of reutericyclin.

In another embodiment, the present invention is a chemical compound that is an analog of tetramic acid. The chemical compound of the invention has antibacterial properties, particularly against gram positive bacteria.

The chemical compound of this embodiment of the invention is an N-substituted, 3-cyano tetramic acid that has the formula shown below as Formula II:

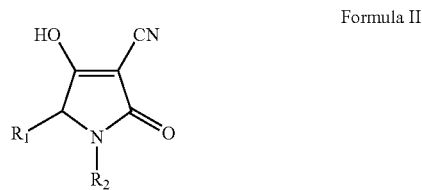

Formula II

A) wherein R1 is:
a) a straight alkyl chain of one to six carbons, such as methyl, ethyl, n-propyl, n-butyl, n-pentyl, or n-hexyl, or branched alkyl chain of one to six carbons,
b) a branched alkyl chain of three to six carbons, such as iso-propyl, iso-butyl, sec-butyl, tert-butyl, or iso-pentyl,
c) an alkyl ring system, such as cyclopropyl, cyclobutyl, cyclopentyl, cyclobutyl methyl, cyclopentyl methyl,
d) an aryl or aryl alkyl ring system, such as phenyl or benzyl, or substituted phenyl or benzyl, wherein examples of substituents are chloro, fluoro, bromo, hydroxyl, methyl, ethyl, methoxy, trifluoromethoxy, morpholinyl, and piperazinyl, or
e) a heteroaryl or heteroaryl alkyl ring system, such as imidazolyl, pyrrolyl, pyridinyl, pyrazinyl, indolyl, furanyl, thienyl, imidazolyl methyl, pyrrolyl methyl, pyridinyl methyl, pyrazinyl methyl, furanyl methyl, indolyl methyl and thienyl methyl, which ring system may or may not be substituted, which substituents may be for example, chloro, fluoro, bromo, hydroxyl, or methoxy, and B) wherein R2 is:
a) a straight alkyl side chain larger than 1 carbon, and preferably larger than 2 carbons,
b) a branched saturated alkyl system, such as iso-propyl, iso-butyl, sec-butyl, tert-butyl, or iso-pentyl,
c) a branched unsaturated alkyl chain of 3 to 16 carbons,
d) a saturated or unsaturated (monocyclic and bicyclic) ring systems of 3 to 16 carbons,
e) an aryl, biaryl, heteroaryl, or bihetero aryl ring system, such as benzyl, substituted benzyl, biphenyl, imidazolyl methyl, pyrrolyl methyl, pyridinyl methyl, pyrazinyl methyl, furanyl methyl, indolyl methyl, or thienyl methyl, wherein substituents may be, for example, chloro, fluoro, bromo, hydroxyl, or methoxy.

In another embodiment, the invention is a method for synthesizing a chemical compound of Formula I or Formula II.

In another embodiment, the invention is a pharmaceutical formulation for parenteral administration containing the chemical compound of the invention as shown in Formula I or Formula II. Such formulation may be in such forms as aqueous or non-aqueous solutions, dispersions, suspensions, or emulsions, or sterile powders for reconstitution into sterile injectable solutions or dispersions. Such solutions, dispersions, suspensions, or emulsions contain, in addition to the chemical compound of the invention, a suitable vehicle in which the chemical compound of the invention is dissolved, dispersed, suspended, or emulsified. Examples of such vehicles include one or more of water, ethanol, polyols such as propylene glycol, polyethylene glycol, and glycerol, vegetable oils, and injectable organic esters.

In another embodiment, the invention is a pharmaceutical formulation for oral administration containing the chemical compound of the invention as shown in Formula I or Formula II. Such pharmaceutical formulations for oral administration include solid and liquid dosage forms.

Solid dosage forms for oral administration include capsules, tablets, powders, and granules. In such solid dosage forms, a chemical compound of the invention is admixed with at least one inert excipient, diluent, or carrier. Suitable excipients, diluents or carriers include materials such as fillers or extenders, binders, humectants, disintegrating agents, solution retarders, absorption accelerators, wetting agents, adsorbents, lubricants, and buffering agents. Solid compositions containing the chemical compound of the invention may also be used, with or without additional excipients, as fillers in soft or hard filled gelatin capsules.

Liquid dosage forms for oral administration include emulsions, solutions, suspensions, syrups, and elixirs. In addition to the compound of the present invention, such liquid dosage form may contain inert diluents, solvents, solubilizing agents, or emulsifiers, such as water, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan. Additional excipients in the liquid dosage form may include, for example, wetting agents, emulsifying and suspending agents, sweetening, flavoring, and perfuming agents.

In another embodiment, the invention is a pharmaceutical formulation for topical administration containing the chemical compound of the invention as shown in Formula I or Formula II. Such topical formulations include solids such as powders, liquids such as solutions and suspensions, foams, and various semi-solids including lotions, creams, and gels, including hydrogels and hydro-alcoholic gels.

In another embodiment, the invention is a method for killing, or inhibiting the growth of, a bacterium. According to this embodiment of the invention, a bacterium is exposed to the chemical compound of the invention as shown in Formula I or Formula II in a concentration and for a time sufficient to kill or inhibit the growth of the bacterium. The exposing of the bacterium to the chemical compound may be in vitro, such as by application of a composition containing the chemical compound to a liquid containing the bacterium or to a surface on which the bacterium is situated. In this way, the chemical compound of the invention may be utilized as an antiseptic or disinfectant.

In another embodiment, the invention is a method for preventing bacterial contamination of medical device surfaces, such as surgical instruments, medical implants and other medical prostheses. According to this embodiment of the invention, the chemical compound as shown in Formula I or Formula II is incorporated into components and materials used to make the medical devices or included in material used to coat medical device surfaces such that the device contains an antimicrobial active component of the invention. In this way the chemical compound of the invention may be utilized to prevent foreign body infections.

Alternatively, the method for killing, or inhibiting the growth of, a bacterium may be in vivo, that is a method for treating or inhibiting the development of a bacterial infection in an individual. According to this embodiment of the invention, the chemical compound of the invention as shown in Formula I or Formula II is administered to an individual in need thereof in a concentration and for a period of time sufficient to kill, or inhibit the growth of, bacteria in or on the body of such individual. The individual may be a human or may be a non-human animal, such as a mammal like a dog, cat, horse, cow, sheep, pig, or goat. Such administration may be topical or systemic, such as parenteral or oral, such as by administering one or more of the formulations described above. An example of topical administration is by application to a wound, such as an abrasion or laceration, such as by applying the topical formulation directly to the wound or by applying a wound dressing in which the chemical compound of the invention is incorporated. Another example of topical administration is for treatment or prophylaxis of skin infections caused by or related to the presence of *Propionibacterium acnes*, including acne vulgaris. It is theorized that at least a portion of the efficacy of the compounds of the invention in treating disorders of the skin, such as acne, is due to the lipophilic nature of the compounds, which enables the compounds to penetrate the oily skin sebum to reach their site of action in the pilosebaceous follicular units. A further example of topical administration is for treatment or prophylaxis in individuals colonized with *Staphylococcus aureus* or other bacteria at sites on the body, such as the anterior nares, hands, wounds, surgical sites and other dermatitides.

The compounds of the invention are particularly useful against microbial biofilms, which are aggregations of bacteria, usually adherent to a surface such as a tissue or an implanted medical device, that are surrounded by an extracellular polysaccharide slime matrix, and exhibit properties that are distinguished from those of planktonic free living microorganisms. The phenotypic (non-genetic) resistance caused by bacteria growing in biofilms is responsible for antibiotic treatment failures in several skin, wound and systemic infections, and is a major cause of chronic infections involving medical implants, such a catheters, mechanical heart valves, and other prostheses. Very few clinically available antibiotics are able to eradicate microbial biofilms. Characteristically, biofilm infections are difficult to eradicate because they are refractory to most antibiotics and are protected from phagocytosis and attack by the immune system. The compounds of the invention are able to disrupt biofilms, such as those caused by gram-positive bacteria.

Accordingly, the compounds of the invention may be used as antibiotics in the treatment and/or prevention of infections associated with microbial biofilms. Examples of biofilm-associated infections that may be treated with the compounds of the invention include otitis media and other ear infections, infections of the eye, dental plaque and dental caries, streptococcal sore throat, skin lesions, cuts and abrasions, impetigo, atoptic dermatitis, wound infections, and those associated with the medical and cosmetic use of a foreign body material such as an implant.

In another embodiment, the invention is a method for reducing the amount of free iron in a wound. In addition to the threat posed by microbial contamination, wound healing is also adversely affected by oxidative stress that is facilitated by the release of iron from hemoglobin and other iron-sulfur proteins. The tetramic acid analogues of the invention act as iron chelators. Accordingly, the present invention provides compounds of Formula I or II which act as both iron chelators and antibiotics. Such compounds may be used as components in wound dressing and wound healing material to improve wound healing process by reducing iron mediated oxidative stress and preventing wound infection by bacteria. According to this embodiment of the invention, a chemical compound of the invention as shown in Formula I or Formula II is topically applied to the wound, such as by directly applying a pharmaceutical formulation of the invention to the wound or by applying a dressing in which the chemical compound of the invention is incorporated to the wound.

In another embodiment, the invention is a method for making a pharmaceutical formulation. According to this embodiment of the invention, the chemical compound of the invention as shown in Formula I or Formula II is combined with one or more suitable excipients, such as those described above, to produce the pharmaceutical formulation.

As described in more detail below, fifteen (15) examples of chemicals compounds of Formula I and eight (8) examples of chemical compounds of Formula II were synthesized and evaluated for their antibacterial properties. The compounds were tested against a number of different bacteria: *Mycobacterium tuberculosis, Escherichia coli, Staphylococcus aureus, Enterococcus faecalis, Bacillus anthracis, Bacillus subtilis, Pseudomonas aeruginosa, Streptococcus pyogenes, Propionibacterium acnes*, and *Streptococcus pneumoniae*. Activity of the compounds of the invention against gram-negative bacteria, such as *E. coli* and *P. aeruginosa*, was not noted, suggesting that the compounds of the invention are primarily effective against gram-positive organisms. Notwithstanding the fact that none of the compounds showed antibacterial activity against the two gram-negative bacteria tested, it is conceived that the compounds may be active against gram-negative bacteria other than those tested.

Of the fifteen compounds of Formula I that were tested, designated compounds 13a to 13o in the Examples that follow, each one showed antibacterial activity against one or more of the bacteria. Of the eight compounds of Formula II that were tested, designated compounds 12a-g and 12p in the Examples that follow, two of the compounds, 12b and 12p, showed antibacterial activity against one or more of the bacteria. Compound 12p was found to be the most active compound against *M. tuberculosis* of the tested compounds of both Formula I and Formula II.

The invention is further illustrated in the following non-limiting examples. For the syntheses as described in Example 1 to 5 below, all reagents and anhydrous solvents were either purchased from Sigma-Aldrich, Acros Organics, Fluka Chemie or Novabiochem. All the reagent-grade solvents used for chromatography were purchased from Fisher Scientific (Suwanee, Ga.) and flash column chromatography silica cartridges were obtained from Biotage Inc. (Lake Forest, Va.). The reactions were monitored by thin-layer chromatography (TLC) on precoated Merck 60 $F_{254}$ silica gel plates and visualized using UV light (254 nm) and Iodine staining. A Biotage FLASH column chromatography system was used to purify the reaction mixtures. All $^1$H NMR spectra were recorded on a Varian INOVA-500 spectrometer. Chemical shifts (δ) are reported in ppm relative to the residual solvent peak or internal standard (tetramethylsilane), and coupling constants (J) are reported in hertz (Hz). Mass spectra were recorded on a Bruker Esquire LCMS using ESI. Optical rotations were measured at room temperature with a Rudolph instruments, Inc. DigiPol 781-T6S Automatic Polarimeter at 589 nm, Dline of sodium. The yields quoted are unoptimized. Purity of the final products was confirmed before antibacterial testing by analytical RP-HPLC on Shimadzu HPLC system. HPLC1 and HPLC3 methods were conducted using Phenomenex Luna 3μ C-18(2) column (50×4.6 mm) at ambient temperature, and a flow rate of 1.0 mL min$^{-1}$. HPLC2 and HPLC4 methods were conducted using Phenomenex Luna 3μ phenyl-hexyl column (50×3.0 mm) at ambient temperature, and a flow rate of 1.0 mL min$^{-1}$. HPLC1: Gradient: solvent A (0.1% TFA in water) and solvent B (acetonitrile): 0-2.00 min 100% A, 2.00-7.00 min 0-100% B (linear gradient), 7.00-8.00 min 100% B, UV detection at 254 nm. HPLC2: Gradient: solvent A (0.1% TFA in water) and solvent B (acetonitrile): 0-2.00 min 100% A, 2.00-7.00 min 0-100% B (linear gradient), 7.00-8.00 min 100% B, UV detection at 254 nm. HPLC3: Gradient: solvent A (0.1% TFA in water) and solvent B (acetonitrile): 0-1.00 min 100% A, 1.00-7.5 min 80-100% B, 7.5-8.00 min 100% B, UV detection at 254 nm. HPLC4: Gradient: solvent A (0.1% TFA in water) and solvent B (acetonitrile): 0-2.00 min 100% A, 2.00-7.5 min 0-100% B, 7.5-8.00 min 100% B, UV detection at 254 nm.

Example 1

General Procedure for Synthesis of Compounds of Formula I (N-substituted 3-acyl Tetramic Acids)

Secondary amines (substituted amino acids) obtained by reductive amination were treated with diketene in the presence of catalytic amounts of Et$_3$N to yield respective beta keto amides. These were subsequently converted into the desired N-substituted 3-acyl tetramic acid.

Example 1a

General Procedure for Synthesis of Secondary Amines

To a stirred solution of amino acid HCl salt (1 equiv) in THF was added MgSO$_4$ (1.7 equiv), aldehyde (2 equiv), and Et$_3$N (1 equiv). The reaction was then left to stir at rt under argon for 5 h. The reaction mixture was then filtered and the eluent evaporated to give the crude imine intermediate. The imine was directly redissolved in methanol and sodium borohydride (2 equiv) was slowly added to the reaction mixture. The reaction was stirred at rt for 30 min, before being quenched with excess 1N NaOH and extracted with ethyl acetate. The ethyl acetate extracts were combined, washed with brine, dried over Na$_2$SO$_4$ and concentrated under vacuum. The residue was purified by flash column chromatography using a petroleum ether to ethyl acetate gradient elution to afford pure products.

Example 1b

General Procedure for Synthesis of N-Substituted 3-acyl Tetramic Acids

To a solution of substituted amino acid (1 equiv) in CH$_2$Cl$_2$ was added diketene (1 equiv) or 50% diketene in dichloromethane and Et₃N (five drops), which was then heated under reflux for 6 h. The reaction mixture was then cooled, diluted with CH₂Cl₂ and washed with dilute hydrochloric acid followed by water. The CH₂Cl₂ fraction was dried over Na₂SO₄ and concentrated. This was then purified by flash column chromatography using a petroleum ether to ethyl acetate gradient elution to afford the desired intermediate products that were then used directly in the next step. To the solution of amide (1 equiv) in methanol (10 mL) was added Amberlyst A-26 resin (4.2 meq/gm, 3 equiv) and the reaction was stirred at rt under argon for 2 h. The product containing resin was filtered and washed with methanol (3×10 mL). The resin was then stirred for 30 min with methanol (10 mL) and TFA (400 µL), filtered and washed with methanol (3×10 mL). Concentration of the eluent afforded the desired products.

Example 2

Secondary Amines Designated 11a to 11p were made as Described in Example 1a and Shown in FIG. 2

Example 2a (2S,3S)-methyl 2-(benzylamino)-3-methylpentanoate (11a)

Synthesized according to the general procedure as described in Example 1a using L-isoleucine methyl ester hydrochloride (1 gm, 5.5 mmol), THF (20 mL) MgSO₄ (1.12 gm, 9.35 mmol), benzaldehyde (1.12 mL, 11.0 mmol), Et₃N (767 µL, 5.5 mmol), sodium borohydride (416 mg, 11.0 mmol), and methanol (30 mL) to give 11a (880 mg, 68%) in FIG. 2. $^1$H NMR (500 MHz, CDCl₃): δ 0.88-0.943 (6H, m), 1.16-1.3 (1H, m), 1.55-1.64 (1H, m), 1.68-1.88 (2H, m), 3.13 (1H, d, J=6.10 Hz), 3.62 (1H, d, J=12.93 Hz), 3.74 (3H, s), 3.84 (1H, d, J=12.93 Hz), 7.24-7.29 (1H, m), 7.31-7.39 (4H, m). ESI-MS: 258.0 (M+23).

Example 2b (S)-methyl 2-(decylamino)-4-methylpentanoate (11b)

Synthesized according to the general procedure as described in Example 1a using L-leucine methyl ester hydrochloride (1 gm, 5.5 mmol), THF (20 mL), MgSO₄ (1.12 gm, 9.35 mmol), decanal (2.06 mL, 11.0 mmol), Et₃N (767 µL, 5.5 mmol), sodium borohydride (416 mg, 11.0 mmol), and methanol (25 mL) to give 11b (800 mg, 51%) in FIG. 2. $^1$H NMR (500 MHz, CDCl₃): δ 0.88-0.98 (9H, m), 1.2-1.37 (15H, m), 1.42-1.54 (4H, m), 1.71 (1H, heptet), 2.42-2.5 (1H, m), 2.53-2.6 (1H, m), 3.29 (1H, t, J=7.32 Hz), 3.74 (3H, s). ESI-MS: 308.1 (M+23).

Example 2c (S)-ethyl 2-(benzylamino)-3-phenylpropanoate (11c)

Synthesized according to the general procedure as described in Example 1a using L-phenylalanine ethyl ester hydrochloride (2 gm, 8.7 mmol), THF (25 mL), MgSO₄ (1.78 gm, 14.79 mmol), benzaldehyde (1.77 mL, 17.4 mmol), Et₃N (1.21 mL, 8.7 mmol), sodium borohydride (658 mg, 17.4 mmol), and methanol (30 mL) to give 11c (1.5 gm, 61%) in FIG. 2. $^1$H NMR (500 MHz, CDCl₃): δ 1.19 (3H, t, J=7.08 Hz), 1.88-2.1 (1H, bs), 3.01 (2H, dd, J=0.97, 7.81 Hz), 3.56 (1H, t, J=6.83 Hz), 3.69 (1H, d, J=13.42 Hz), 3.85 (1H, d, J=13.18 Hz), 4.13 (2H, q, J=7.32 Hz), 7.18-7.22 (2H, m), 7.23-7.33 (8H, m). ESI-MS: 284.0 (M+1).

Example 2d (S)-methyl 2-(3-methoxybenzylamino)-4-methylpentanoate (11d)

Synthesized according to the general procedure as described in Example 1a using L-leucine methyl ester hydrochloride (2 gm, 11.0 mmol), THF (30 mL), MgSO₄ (2.24 gm, 18.7 mmol), m-anisaldehyde (2.67 mL, 22.0 mmol), Et₃N (1.53 mL, 11.0 mmol), sodium borohydride (833 mg, 22.0 mmol), and methanol (40 mL) to give 11d (1.7 gm, 58%) in FIG. 2. $^1$H NMR (500 MHz, CD₃OD): δ 0.86 (3H, d, J=6.59 Hz), 0.92 (3H, d, J=6.59 Hz), 1.5 (2H, dt, J=2.68, 7.32 Hz), 1.71 (1H, heptet), 3.3 (1H, t, J=7.32 Hz), 3.59 (1H, d, J=13.18 Hz), 3.72 (3H, s), 3.76 (1H, d, J=12.93 Hz), 3.8 (3H, s), 6.82 (1H, dd, J=2.44, 8.29 Hz), 6.89 (1H, d, J=7.56 Hz), 6.93, (1H, t, J=1.95 Hz), 7.23 (1H, t, J=7.81). ESI-MS: 288.2 (M+23).

Example 2e (S)-methyl 2-(4-fluorobenzylamino)-4-methylpentanoate (11e)

Synthesized according to the general procedure as described in Example 1a using L-leucine methyl ester hydrochloride (2 gm, 11.0 mmol), THF (30 mL), MgSO₄ (2.24 gm, 18.7 mmol), 4-fluorobenzaldehyde (2.37 mL, 22.0 mmol), Et₃N (1.53 mL, 11.0 mmol), sodium borohydride (833 mg, 22.0 mmol), and methanol (40 mL) to give 11e (1.3 gm, 47%) in FIG. 2. $^1$H NMR (500 MHz, CDCl₃): δ 0.84 (3H, d, J=6.59 Hz), 0.9 (3H, d, J=6.59 Hz), 1.47-1.58 (2H, m), 1.76 (1H, heptet), 3.3 (1H, t, J=7.32 Hz), 3.63 (1H, d, J=12.93 Hz), 3.72 (3H, s), 3.81 (1H, d, J=12.93 Hz), 6.99 (2H, t, J=8.78 Hz), 7.32 (2H, dd, J=5.37, 8.3 Hz). ESI-MS: 276.2 (M+23).

Example 2f (R)-methyl 2-(4-fluorobenzylamino)-4-methylpentanoate (11f)

Synthesized according to the general procedure as described in Example 1a using D-leucine methyl ester hydrochloride (2 gm, 11.0 mmol), THF (30 mL), MgSO₄ (2.24 gm, 18.7 mmol), 4-fluorobenzaldehyde (2.37 mL, 22.0 mmol), Et₃N (1.53 mL), sodium borohydride (833 mg, 22.0 mmol), and methanol (40 mL) to give 11f (1.72 gm, 62%) in FIG. 2. $^1$H NMR (500 MHz, CDCl₃): δ 0.84 (3H, d, J=6.59 Hz), 0.91 (3H, d, J=6.59 Hz), 1.4-1.52 (2H, m), 1.64-1.72 (1H, bs), 1.77 (1H, heptet), 3.27 (1H, t, J=7.41 Hz), 3.56 (1H, d, J=12.9 Hz), 3.72 (3H, s), 3.77 (1H, d, J=12.9 Hz), 6.99 (2H, t, J=8.78 Hz), 7.28 (2H, dd, J=5.49, 8.51 Hz). ESI-MS: 276.0 (M+23).

Example 2g (R)-methyl 2-(benzylamino)-3-phenylpropanoate (11g)

Synthesized according to the general procedure as described in Example 1a using D-phenylalanine methyl ester hydrochloride (2 gm, 9.2 mmol), THF (25 mL), MgSO₄ (1.87 gm, 15.6 mmol), benzaldehyde (1.88 mL, 18.5 mmol), Et₃N (1.28 mL, 9.2 mmol), sodium borohydride (699 mg, 18.5 mmol), and methanol (30 mL) to give 11g (1.8 gm, 72%) in FIG. 2. $^1$H NMR (500 MHz, CD$_3$OD): δ 2.96 (2H, d, J=6.59 Hz), 3.53 (1H, t, J=7.08 Hz), 3.6 (3H, s), 3.63 (1H, d, J=12.93 Hz), 3.77 (1H, d, J=12.93 Hz), 7.13-7.18 (2H, m), 7.19-7.32 (8H, m). ESI-MS: 292.2 (M+23).

Example 2h (S)-ethyl 2-(ethylamino)-3-phenylpropanoate (11h)

Synthesized according to the general procedure as described in Example 1a using L-phenylalanine ethyl ester hydrochloride (2 gm, 8.7 mmol), THF (25 mL), MgSO$_4$ (1.77 gm, 14.79 mmol), acetaldehyde (983 μL, 17.4 mmol), Et$_3$N (1.21 mL, 8.7 mmol), sodium borohydride (658 mg, 17.4 mmol), and methanol (30 mL) to give 11h (900 mg, 47%) in FIG. 2. $^1$H NMR (500 MHz, CDCl$_3$): δ 1.1 (3H, t, J=7.13 Hz), 1.15 (3H, t, J=7.13 Hz), 1.42-1.7 (1H, bs), 2.46-2.73 (2H, m), 2.96 (2H, dq, J=7.44, 13.42 Hz), 3.53 (1H, t, J=6.88 Hz), 4.1 (2H, q, J=7.13 Hz), 7.16-7.38 (5H, m). ESI-MS: 244.1 (M+23).

Example 2i (S)-methyl 2-(decylamino)-3-methylbutanoate (11i)

Synthesized according to the general procedure as described in Example 1a using L-valine methyl ester hydrochloride (1.5 gm, 8.9 mmol), THF (25 mL), MgSO$_4$ (1.81 gm, 15.13 mmol), decanal (3.36 mL, 17.89 mmol), Et$_3$N (1.24 mL, 8.9 mmol), sodium borohydride (677 mg, 17.89 mmol), and methanol (25 mL) to give 11i (1.22 gm, 50%) in FIG. 2. $^1$H NMR (500 MHz, CDCl$_3$): δ 0.87 (3H, t, J=7.07 Hz), 0.92 (3H, d, J=7.37 Hz), 0.94 (3H, d, J=6.83 Hz), 1.2-1.5 (17H, m), 1.88 (1H, sextet), 2.37-2.44 (1H, m), 2.5-2.8 (1H, m), 2.97 (1H, d, J=6.34 Hz), 3.74 (3H, s). ESI-MS: 294.3 (M+23).

Example 2j (S)-methyl 2-(butylamino)-4-methylpentanoate (11j)

Synthesized according to the general procedure as described in Example 1a using L-leucine methyl ester hydrochloride (1.5 gm, 8.25 mmol), THF (25 mL), MgSO$_4$ (1.68 gm, 14.02 mmol), butyraldehyde (1.45 mL, 16.5 mmol), Et$_3$N (1.14 mL, 8.25 mmol), sodium borohydride (625 mg, 16.5 mmol), and methanol (25 mL) to give 11j (450 mg, 27%) in FIG. 2. $^1$H NMR (500 MHz, CDCl$_3$): δ 0.86-0.98 (9H, m), 1.24-1.52 (7H, m), 1.64-1.74 (1H, heptet), 2.4-2.48 (1H, m), 2.52-2.6 (1H, m), 3.27 (1H, t, J=7.33 Hz), 3.71 (3H, s). ESI-MS: 224.1 (M+23).

Example 2k (S)-methyl 2-(biphenyl-4-ylmethylamino)-4-methylpentanoate (11k)

Synthesized according to the general procedure as described in Example 1a using L-leucine methyl ester hydrochloride (1.0 gm, 5.5 mmol), THF (25 mL), MgSO$_4$ (1.12 gm, 9.35 mmol), biphenyl carboxaldehyde (2.0 g, 11.0 mmol), Et$_3$N (767 μL, 5.5 mmol), sodium borohydride (417 mg, 11.0 mmol), and methanol (20 mL) to give 11k (750 mg, 44%) in FIG. 2. $^1$H NMR (500 MHz, CDCl$_3$): δ 0.86 (3H, d, J=6.59 Hz), 0.92 (3H d, J=6.59 Hz), 1.49 (2H, dt, J=3.17, 7.07 Hz), 1.7-1.76 (1H, bs), 1.8 (1H, heptet), 3.33 (1H, t, J=7.56 Hz), 3.65 (1H, d, J=12.93 Hz), 3.72 (3H, s), 3.85 (1H, d, J=13.18 Hz), 7.32 (1H, t, J=7.56 Hz), 7.38-7.42 (4H, m), 7.54 (2H, d, J=7.81 Hz), 7.58 (2H, d, J=7.32 Hz). ESI-MS: 312.4 (M+1).

Example 2l (2S)-methyl 2-((6,6-dimethylbicyclo[3.1.1]hept-2-en-2-yl)methylamino)-4-methylpentanoate (11l)

Synthesized according to the general procedure as described in Example 1a using L-leucine methyl ester hydrochloride (2.0 gm, 11.0 mmol), THF (25 mL), MgSO$_4$ (2.24 gm, 18.7 mmol), (1R)-(−) myrtenal (3.30 g, 22.0 mmol), Et$_3$N (1.54 mL, 11.0 mmol), sodium borohydride (832 mg, 22.0 mmol), and methanol (20 mL) to give 11l (1.56 gm, 51%) in FIG. 2. $^1$H NMR (500 MHz, CDCl$_3$): δ 0.82 (3H, s), 0.89 (3H, d, J=6.59 Hz), 0.91 (3H d, J=6.83 Hz), 1.15 (1H, d, J=8.54 Hz), 1.27 (3H, s), 1.38-1.54 (3H, m), 1.68 (1H, m), 2.08 (2H, d, J=5.37 Hz), 2.24 (2H, q, J=16.11 Hz), 2.32-2.4 (1H, m), 2.94 (1H, dd, J=1.7, 13.91 Hz), 3.08 (1H, dd, J=1.46, 13.67 Hz), 3.29 (1H, t, J=7.32 Hz), 3.71 (3H, s), 5.36 (1H, s). ESI-MS: 302.2 (M+23).

Example 2m (2S)-methyl 2-(3,7-dimethyloct-6-enylamino)-4-methylpentanoate (11m)

Synthesized according to the general procedure as described in Example 1a using L-leucine methyl ester hydrochloride (2.0 gm, 11.0 mmol), THF (30 mL), MgSO$_4$ (2.24 gm, 18.7 mmol), (±) citronellal (3.95 mL, 22.0 mmol), Et$_3$N (1.54 mL, 11.0 mmol), sodium borohydride (832 mg, 22.0 mmol), and methanol (20 mL) to give 11m (2.3 gm, 74%) in FIG. 2. $^1$H NMR (500 MHz, CDCl$_3$): δ 0.86 (3H, d, J=6.34 Hz), 0.9 (3H, d, J=6.59 Hz), 0.92 (3H d, J=6.83 Hz), 1.1-1.2 (1H, m), 1.24-1.36 (3H, m), 1.42-1.54 (4H, m), 1.59 (3H, m), 1.67 (4H, m), 1.9-2.08 (2H, m), 2.4-2.62 (2H, m), 3.27 (1H, t, J=7.32 Hz), 3.71 (3H, s), 5.08 (1H, t, J=7.32 Hz). ESI-MS: 306.3 (M+23).

Example 2n (S)-ethyl 2-(decylamino)-3-phenylpropanoate (11n)

Synthesized according to the general procedure as described in Example 1a using L-phenyl alanine ethyl ester hydrochloride (1.0 gm, 4.35 mmol), THF (20 mL), MgSO$_4$ (522 mg, 4.35 mmol), decanal (817 μL, 4.35 mmol), Et$_3$N (606 μL, 4.35 mmol), sodium borohydride (330 mg, 8.7 mmol), and methanol (20 mL) to give 11n (270 mg, 19%) in FIG. 2. $^1$H NMR (500 MHz, CDCl$_3$): δ 0.88 (3H, d, J=7.08 Hz), 1.14 (3H, t, J=7.32 Hz), 1.2-1.32 (14H, m), 1.34-1.5 (3H, m), 2.5-2.55 (1H, m), 2.52-2.6 (1H, m), 2.9 (1H, dd, J=7.56, 13.42 Hz), 2.97 (1H, dd, J=6.59, 13.42 Hz), 3.48 (1H, t, J=6.83 Hz), 4.08 (2H, q, J=7.32 Hz), 7.18 (2H, d, J=7.32 Hz), 7.22 (1H, d, J=0.73 Hz), 7.24-7.3 (2H, m). ESI-MS: 334.4 (M+1).

Example 2o (R)-methyl 2-(decylamino)-4-methylpentanoate (11o)

Synthesized according to the general procedure as described in Example 1a using D-leucine methyl ester hydrochloride (1.5 gm, 8.25 mmol), THF (20 mL), MgSO$_4$ (1.68 gm, 14.02 mmol), decanal (3.1 mL, 16.5 mmol), Et$_3$N (1.15 mL, 8.25 mmol), sodium borohydride (624 mg, 16.5 mmol), and methanol (30 mL) to give 11o (950 mg, 40%) in FIG. 2. $^1$H NMR (500 MHz, CDCl$_3$): δ 0.86-0.96 (9H, m), 1.2-1.34 (16H, m), 1.38-1.52 (4H, m), 1.69 (1H, heptet), 2.39-2.48 (1H, m), 2.5-2.58 (1H, m), 3.27 (1H, t, J=7.08 Hz), 3.71 (3H, s). ESI-MS: 308.1 (M+23).

Example 2p (2S,3S)-methyl 2-(furan-2-ylmethylamino)-3-methylpentanoate (11p)

Synthesized according to the general procedure as described in Example 1a using L-isoleucine methyl ester hydrochloride (2.5 gm, 1 equiv), THF (30 mL), MgSO$_4$ (2.8 gm, 1.7 equiv), 2-furaldehyde (2.27 mL, 2 equiv), and Et$_3$N (1.91 mL, 1 equiv), sodium borohydride (1.04 gm, 2 equiv), and methanol (40 mL) to give 11p (2.2 gm, 71%) in FIG. 2. $^1$H NMR (500 MHz, CDCl$_3$): δ 0.86-0.92 (6H, m), 1.16-1.26 (1H, m), 1.48-1.58 (1H, m), 1.68-1.74 (1H, m), 1.78-1.98 (1H, bs), 3.16 (1H, d, J=5.85 Hz), 3.67 (1H, d, J=14.15 Hz), 3.71 (3H, s), 3.82 (1H, d, J=14.4 Hz), 6.19 (1H, d, J=3.17 Hz), 6.32 (1H, d, J=2.68 Hz), 7.37 (1H, d, J=1.95 Hz). ESI-MS: 248.1 (M+23).

Example 3

Synthesis of N-substituted 3-acyl Tetramic Acids

Figure 3:
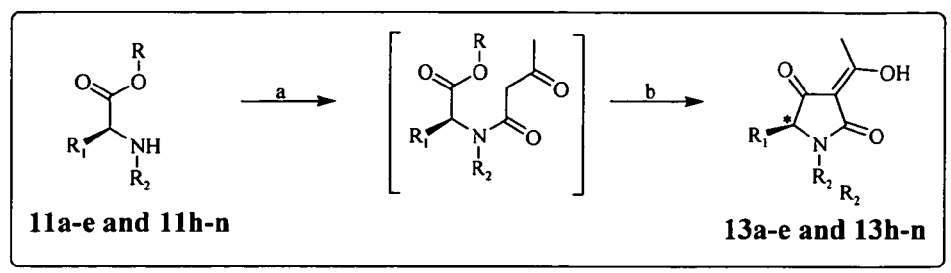
FIG. 3 shows the synthetic scheme for making N-substituted 3-acyl tetramic acid derivatives from amino acid ester salts. (A) shows synthesis starting with N-substituted L-amino acid esters. (B) shows synthesis starting with N-substituted D-amino acid esters. Reagents and conditions for the synthetic schemes were as follows: Reagents: (a) Diketene or 50% diketene in $CH_2Cl_2$, $CH_2Cl_2$, $Et_3N$, 6 hours, reflux (b) (i) Amberlyst A-26 hydroxide resin, MeOH, room temperature, 2 hours, (ii) MeOH, TFA, room temperature, 20 minutes. * Indicates racemizations might have occurred during synthesis.
Figure 3:
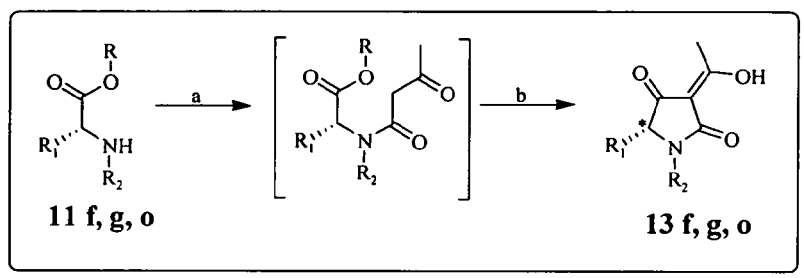
Figure 4A:
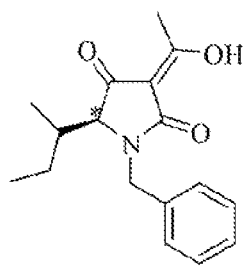
FIG. 4 shows the chemical structure of compounds of Formula I designated 13a to 13p, as follows. 13a is (S,Z)-1-benzyl-5-sec-butyl-3-(1-hydroxyethylidene)pyrrolidine-2,4-dione. 13b is (S,Z)-1-decyl-3-(1-hydroxyethylidene)-5-isobutylpyrrolidine-2,4-dione. 13c is (S,Z)-1,5-dibenzyl-3-(1-hydroxyethylidene)pyrrolidine-2,4-dione. 13d is (S,Z)-3-(1-hydroxyethylidene)-5-isobutyl-1-(3-methoxybenzyl) pyrrolidine-2,4-dione. 13e is (S,Z)-1-(4-fluorobenzyl)-3-(1-hydroxyethylidene)-5-isobutylpyrrolidine-2,4-dione. 13f is (R,Z)-1-(4-fluorobenzyl)-3-(1-hydroxyethylidene)-5-isobutylpyrrolidine-2,4-dione. 13g is (R,Z)-1,5-dibenzyl-3-(1-hydroxyethylidene)pyrrolidine-2,4-dione. 13h is (S,Z)-5-benzyl-1-ethyl-3-(1-hydroxyethylidene)pyrrolidine-2,4-dione. 13i is (S,Z)-1-decyl-3-(1-hydroxyethylidene)-5-isopropylpyrrolidine-2,4-dione. 13j is (S,Z)-1-butyl-3-(1-hydroxyethylidene)-5-isobutylpyrrolidine-2,4-dione. 13k is (S,Z)-1-(biphenyl-4-ylmethyl)-3-(1-hydroxyethylidene)-5-isobutylpyrrolidine-2,4-dione. 13l is (5S,Z)-1-((6,6-dimethylbicyclo[3.1.1]hept-2-en-2-yl)methyl)-3-(1-hydroxyethylidene)-5-isobutylpyrrolidine-2,4-dione. 13m is (5S,Z)-1-(3,7-dimethyloct-6-enyl)-3-(1-hydroxyethylidene)-5-isobutylpyrrolidine-2,4-dione. 13n is (S,Z)-5-benzyl-1-decyl-3-(1-hydroxyethylidene)pyrrolidine-2,4-dione. 13o is (R,Z)-1-decyl-3-(1-hydroxyethylidene)-5-isobutylpyrrolidine-2,4-dione.
Figure 4A:
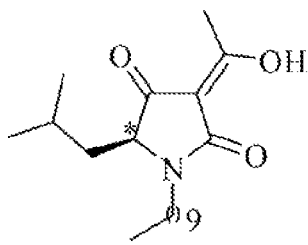
Figure 4A:
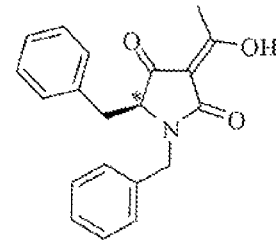
Figure 4A:
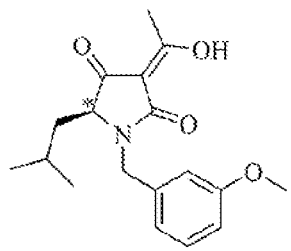
Figure 4A:
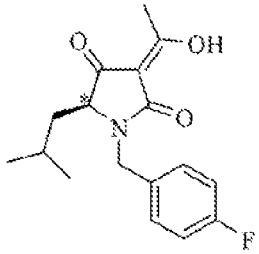
Figure 4A:
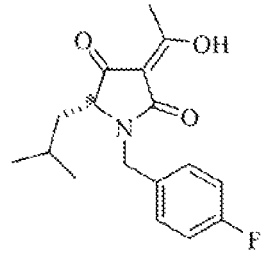
Figure 4A:
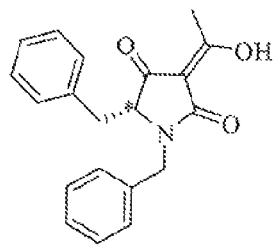
Figure 4A:
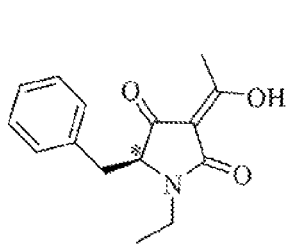
Figure 4A:
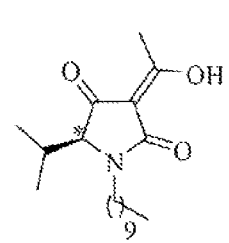
Figure 4A:
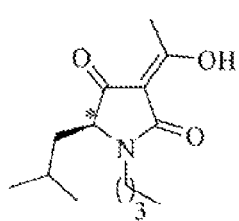
Figure 4A:
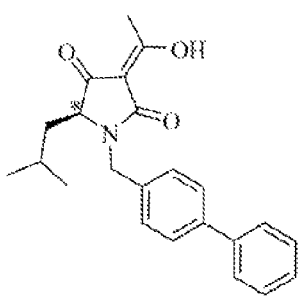
Figure 4A:
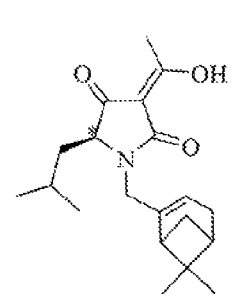
Figure 4B:
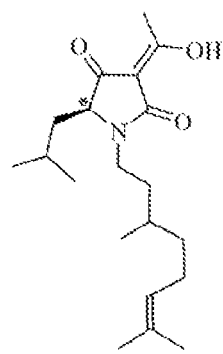
Figure 4B:
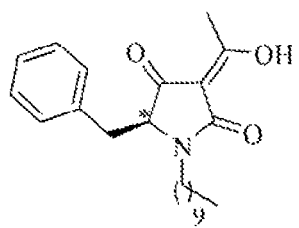
Figure 4B:
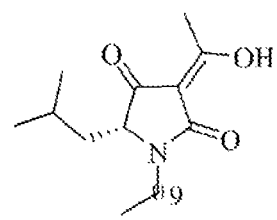

N-substituted 3-acyl tetramic acids were synthesized in the scheme shown in FIGS. 3a and 3b, utilizing the secondary amines of FIG. 2 as starting material. The respective N-substituted 3-acyl tetramic acids were designated 13a to 13o, the structures of which are shown in FIG. 4.

Example 3a (S,Z)-1-benzyl-5-sec-butyl-3-(1-hydroxyethylidene)pyrrolidine-2,4-dione (13a)

Synthesized according to the general procedure as described in Example 1b using (2S,3S)-methyl 2-(benzylamino)-3-methylpentanoate 11a of Example 2a (500 mg, 2.12 mmol), CH$_2$Cl$_2$ (30 mL), diketene (165 μL, 2.12 mmol) and Et$_3$N (five drops) to give amide (420 mg, 62%). To the solution of amide (420 mg, 1.31 mmol) in methanol (10 mL) was added Amberlyst A-26 resin (936 mg, 3.93 mmol) and the reaction was carried out as described in Example 1b to give 13a (310 mg, 82%). $^1$H NMR (500 MHz, CDCl$_3$): δ 0.78-0.94 (6H, m), 1.5-1.66 (2H, m), 1.9-2.2 (1H, m), 2.46 (2.2H, s, Me 3-acetyl major tautomer), 2.58 (0.8H, s, Me 3-acetyl minor tautomer), 3.59 and 3.76 (1H, 2ds, J=3.29 Hz), 3.94-4.4 (1H, m), 5.24-5.38 (1H, m), 7.22-7.28 (2H, m), 7.31-7.42 (3H, m). $^1$H NMR (500 MHz, CD$_3$OD): δ 0.76 (3H, d, J=6.86 Hz), 0.87 (3H, t, J=7.41 Hz), 1.46-1.66 (2H, m), 1.9-2.4 (1H, m), 2.47 (3H, s), 3.72-3.8 (1H, bs), 4.21 (0.81H, d, J=15.1 Hz) and 4.35 (0.19H, d, J=15.31 Hz), 5.01 (0.81H, d, J=15.37 Hz), 5.12 (0.19H, d, J=15.1 Hz), 7.29-7.41 (5H, m). ESI-MS: 286 (M−1). IR $v_{max}$ (cm$^{-1}$): 1709.26, 1615.06 cm$^{-1}$. $[α]_D^{27.3}$−87.0 (c=1%, MeOH). HPLC1: $t_R$ 7.17 min, Purity >99%. HPLC2: $t_R$ 6.10 min, Purity 97%.

Example 3b (S,Z)-1-decyl-3-(1-hydroxyethylidene)-5-isobutylpyrrolidine-2,4-dione (13b)

Synthesized according to the general procedure as described in Example 1b using (S)-methyl 2-(decylamino)-4-methylpentanoate 11b of Example 2b (500 mg, 1.75 mmol), CH$_2$Cl$_2$ (30 mL), diketene (136 μL, 1.75 mmol) and Et$_3$N (five drops) to give amide (280 mg, 43%). To the solution of amide (280 mg, 0.758 mmol) in methanol (10 mL) was added Amberlyst A-26 resin (540 mg, 2.276 mmol) and the reaction was carried out as described in Example 1b to give 13b (220 mg, 86%). $^1$H NMR (500 MHz, CDCl$_3$): δ 0.88-0.98 (9H, m), 1.26-1.36 (14H, m), 1.48-1.74 (4H, m), 1.89 (1H, heptet), 2.46 (2.62H, s, Me 3-acetyl major tautomer), 2.54 (0.38H, s, Me 3-acetyl minor tautomer), 2.94-3.02 (1H, m), 3.8 (1H, dd, J=4.39, 7.14 Hz), 3.82-3.92 (1H, m). ESI-MS: 360.1 (M+23). IR $v_{max}$ (cm$^{-1}$): 2924.68, 1624.89 cm$^{-1}$. $[α]_D^{27.7}$+2.1 (c=1%, MeOH). HPLC3: $t_R$ 5.36 min, Purity: 99%. HPLC4: $t_R$ 7.27 min, Purity 98%.

Example 3c (S,Z)-1,5-dibenzyl-3-(1-hydroxyethylidene)pyrrolidine-2,4-dione (13c)

Synthesized according to the general procedure as described in Example 1b using (S)-ethyl 2-(benzylamino)-3-phenylpropanoate 11c of Example 2c (400 mg, 1.41 mmol), CH$_2$Cl$_2$ (30 mL), diketene (109 μL, 1.41 mmol) and Et$_3$N (five drops) to give amide (320 mg, 62%). To the solution of amide (300 mg, 0.817 mmol) in methanol (10 mL) was added Amberlyst A-26 resin (583 mg, 2.452 mmol) and the reaction was carried out as described in Example 1b to give 13c (210 mg, 80%). $^1$H NMR (500 MHz, CD$_3$OD): δ 2.38 (3H, s), 3.1 (1H, dd, J=4.66, 14.55 Hz), 3.24 (1H, dd, J=4.66, 14.55 Hz), 3.9-4.0 (1H, bs), 4.17 (1H, d, J=15.1 Hz), 5.17 (1H, d, J=15.1 Hz), 7.12 (2H, dd, J=1.64, 7.41 Hz), 7.17-7.22 (2H, m), 7.22-7.28 (3H, m), 7.28-7.37 (3H, m). ESI-MS: 344 (M+23). IR max (cm$^{-1}$): 1612.49 cm$^{-1}$. $[α]_D^{27.9}$−60.0 (c=1%, MeOH). HPLC1: $t_R$ 6.97 min, Purity 94%. HPLC2: $t_R$ 6.07 min, Purity 95%.

Example 3d (S,Z)-3-(1-hydroxyethylidene)-5-isobutyl-1-(3-methoxybenzyl)pyrrolidine-2,4-dione (13d)

Synthesized according to the general procedure as described in Example 1b using (S)-methyl 2-(3-methoxybenzylamino)-4-methylpentanoate 11d of Example 2d (420 mg, 1.58 mmol), CH$_2$Cl$_2$ (20 mL), 50% diketene in CH$_2$Cl$_2$ (266 μL, 1.58 mmol) and Et$_3$N (five drops), to give amide (480 mg, 87%). To the solution of amide (440 mg, 1.25 mmol) in methanol (10 mL) was added Amberlyst A-26 resin (897 mg, 3.77 mmol) and the reaction was carried out as described in Example 1b to give 13d (280 mg, 70%). $^1$H NMR (500 MHz, CD$_3$OD): δ 0.8 (3H, d, J=6.59 Hz), 0.86 (3H, d, J=6.59 Hz), 1.61-1.72 (2H, m), 1.79 (1H, heptet), 2.47 (3H, s), 3.71 (1H, dd, J=2.19, 6.59 Hz), 3.79 (3H, s), 4.21 (1H, d, J=15.37 Hz), 5.04 (1H, d, J=15.1 Hz), 6.84-6.9 (3H, m), 7.27 (1H, t, J=7.96 Hz). ESI-MS: 316.1 (M−1). IR $v_{max}$ (cm$^{-1}$): 1610.24 cm$^{-1}$. $[α]_D^{28}$+6.0 (c=1%, MeOH). HPLC1: $t_R$ 7.12 min, Purity 84%. HPLC2: $t_R$ 6.05 min, Purity 98%.

Example 3e (S,Z)-1-(4-fluorobenzyl)-3-(1-hydroxyethylidene)-5-isobutylpyrrolidine-2,4-dione (13e)

Synthesized according to the general procedure as described in Example 1b using (S)-methyl 2-(4-fluorobenzylamino)-4-methylpentanoate 11e of Example 2e (520 mg, 2.05 mmol), CH$_2$Cl$_2$ (20 mL), 50% diketene in CH$_2$Cl$_2$ (345 µL, 2.05 mmol) and Et$_3$N (five drops), to give amide (480 mg, 69%). To the solution of amide (460 mg, 1.363 mmol) in methanol (10 mL) was added Amberlyst A-26 resin (974 mg, 4.09 mmol) and the reaction was carried out as described in Example 1b to give 13e (260 mg 63%). $^1$H NMR (500 MHz, CD$_3$OD): δ 0.81 (3H, d, J=6.34 Hz), 0.87 (3H, d, J=6.83 Hz), 1.61-1.72 (2H, m), 1.78 (1H, heptet), 2.47 (3H, s), 3.68-3.78 (1H, bs), 4.26 (1H, d, J=15.37 Hz), 5.04 (1H, d, J=15.13 Hz), 7.1 (2H, t, J=8.54 Hz), 7.34 (2H, dd, J=5.37, 8.54 Hz). ESI-MS: 304 (M−1). IR ν$_{max}$ (cm$^{-1}$): 1615.17 cm$^{-1}$. [α]$_D^{24.7}$−45.4 (c=1%, MeOH). HPLC1: t$_R$ 7.15 min, Purity: 91%. HPLC2: t$_R$ 6.11 min, Purity >99%.

Example 3f (R,Z)-1-(4-fluorobenzyl)-3-(1-hydroxyethylidene)-5-isobutylpyrrolidine-2,4-dione (13f)

Synthesized according to the general procedure as described in Example 1b using (R)-methyl 2-(4-fluorobenzylamino)-4-methylpentanoate 11f of Example 2f (520 mg, 2.05 mmol), CH$_2$Cl$_2$ (20 mL), 50% diketene in CH$_2$Cl$_2$ (345 µL, 2.05 mmol) and Et$_3$N (five drops), to give amide (410 mg, 59%). To the solution of amide (410 mg, 1.215 mmol) in methanol (10 mL) was added Amberlyst A-26 resin (868 mg, 3.645 mmol) and the reaction was carried out as described in Example 1b to give 13f (230 mg, 62%). $^1$H NMR (500 MHz, CD$_3$OD): δ 0.81 (3H, d, J=6.59 Hz), 0.87 (3H, d, J=6.59 Hz), 1.61-1.72 (2H, m), 1.78 (1H, heptet), 2.48 (3H, s), 3.68-3.78 (1H, bs), 4.26 (1H, d, J=15.37 Hz), 5.04 (1H, d, J=15.37 Hz), 7.1 (2H, t, J=8.78 Hz), 7.34 (2H, dd, J=5.21, 8.51 Hz). ESI-MS: 304 (M−1). IR ν$_{max}$ (cm$^{-1}$): 1615.14 cm$^{-1}$. [α]$_D^{23.8}$+67.8 (c=1%, MeOH). HPLC1: t$_R$ 7.09 min, Purity 93%. HPLC2: t$_R$ 6.1 min, Purity 93%.

Example 3g (R,Z)-1,5-dibenzyl-3-(1-hydroxyethylidene)pyrrolidine-2,4-dione (13g)

Synthesized according to the general procedure as described in Example 1b using (R)-methyl 2-(benzylamino)-3-phenylpropanoate 11g of Example 2g (500 mg, 1.85 mmol), CH$_2$Cl$_2$ (30 mL), 50% diketene in CH$_2$Cl$_2$ (311 µL, 1.85 mmol) and Et$_3$N (five drops) to give amide (520 mg, 79%). To the solution of amide (520 mg, 1.47 mmol) in methanol (10 mL) was added Amberlyst A-26 resin (1.05 g, 4.41 mmol) the reaction was carried out as described in Example 1b to give 13g (380 mg, 80%). $^1$H NMR (500 MHz, CD$_3$OD): δ 2.38 (3H, s), 3.1 (1H, dd, J=4.66, 14.55 Hz), 3.24 (1H, dd, J=4.66, 14.55 Hz), 3.9-4.0 (1H, bs), 4.17 (1H, d, J=15.1 Hz), 5.17 (1H, d, J=15.1 Hz), 7.12 (2H, dd, J=1.30, 7.14 Hz), 7.17-7.22 (2H, m), 7.22-7.28 (3H, m), 7.28-7.37 (3H, m). ESI-MS: 322.1 (M+1). IR ν$_{max}$ (cm$^{-1}$): 1612.2 cm$^{-1}$. [α]$_D^{26.8}$+67.5 (c=1%, MeOH). HPLC1: t$_R$ 6.95 min, Purity: 91%. HPLC2: t$_R$ 6.07 min, Purity: 99%.

Example 3h (S,Z)-5-benzyl-1-ethyl-3-(1-hydroxyethylidene)pyrrolidine-2,4-dione (13h)

Synthesized according to the general procedure as described in Example 1b using (S)-ethyl 2-(ethylamino)-3-phenylpropanoate 11h of Example 2h (300 mg, 1.35 mmol), CH$_2$Cl$_2$ (20 mL), diketene (105 µL, 1.35 mmol) and Et$_3$N (five drops) to give amide (160 mg, 39%). To the solution of amide (150 mg, 0.49 mmol) in methanol (10 mL) was added Amberlyst A-26 resin (350 mg, 1.47 mmol) and the reaction was carried out as described in Example 1b to give 13h (102 mg, 80%). $^1$H NMR (500 MHz, CD$_3$OD): δ 1.15 (3H, t, J=7.14 Hz), 2.33 (3H, s), 3.1-3.26 (3H, m), 3.88 (1H, sextet), 4.22-4.32 (1H, bs), 7.1-7.16 (2H, m), 7.14-7.29 (3H, m). ESI-MS: 258 (M−1). IR ν$_{max}$ (cm$^{-1}$): 1603.61 cm$^{-1}$. [α]$_D^{27.6}$+0.5 (c=1%, MeOH). HPLC1: t$_R$ 6.32 min, Purity >99%. HPLC2: t$_R$ 3.92 min, Purity >99%.

Example 3i (S,Z)-1-decyl-3-(1-hydroxyethylidene)-5-isopropylpyrrolidine-2,4-dione (13i)

Synthesized according to the general procedure as described in Example 1b using (S)-methyl 2-(decylamino)-3-methylbutanoate 11i of Example 2i (1 g, 3.68 mmol), CH$_2$Cl$_2$ (30 mL), 50% diketene in CH$_2$Cl$_2$ (620 µL, 3.68 mmol) and Et$_3$N (five drops) to give amide (589 mg, 45%). To the solution of amide (350 mg, 0.985 mmol) in methanol (10 mL) was added Amberlyst A-26 resin (704 mg, 2.95 mmol) and the reaction was carried out as described in Example 1b to give 13i (220 mg, 69%). $^1$H NMR (500 MHz, CD$_3$OD): δ 0.86 (3H, d, J=7.08 Hz), 0.92 (3H, t, J=7.08 Hz), 1.17 (3H, d, J=7.07 Hz), 1.28-1.4 (14H, m), 1.5-1.7 (2H, m), 2.2-2.32 (1H, m), 2.43 (3H, s), 3.06-3.12 (1H, m), 3.76-3.86 (2H, m). ESI-MS: 322.1 (M−1). IR ν$_{max}$ (cm$^{-1}$): 2924, 1623 cm$^{-1}$. [α]$_D^{24.7}$−43.5 (c=1%, CHCl$_3$). HPLC3: t$_R$ 4.86 min, Purity 99%. HPLC4: t$_R$ 7.15 min, Purity 98%.

Example 3j (S,Z)-1-butyl-3-(1-hydroxyethylidene)-5-isobutylpyrrolidine-2,4-dione (13j)

Synthesized according to the general procedure as described in Example 1b using (S)-methyl 2-(butylamino)-4-methylpentanoate 11j of Example 2j (420 mg, 2.08 mmol), CH$_2$Cl$_2$ (20 mL), 50% diketene in CH$_2$Cl$_2$ (351 µL, 2.08 mmol) and Et$_3$N (five drops) to give amide (410 mg, 69%). To the solution of amide (370 mg, 1.29 mmol) in methanol (10 mL) was added Amberlyst A-26 resin (926 mg, 3.88 mmol) and the reaction was carried out as described in Example 1b to give 13j (230 mg, 70%). $^1$H NMR (500 MHz, CD$_3$OD): δ 0.92 (3H, d, J=6.59 Hz), 0.94-1.02 (6H, m), 1.3-1.42 (2H, m), 1.5-1.68 (2H, m), 1.68-1.78 (2H, m), 1.84 (1H, heptet), 2.44 (3H, s), 3.04-3.12 (1H, m), 3.78-3.86 (1H, m), 3.94-4 (1H, bs). ESI-MS: 251.9 (M−1). IR ν$_{max}$ (cm$^{-1}$): 2958, 1619 cm$^{-1}$. [α]$_D^{24.1}$−35.4 (c=1%, CHCl$_3$). HPLC3: t$_R$ 2.55 min, Purity 97%. HPLC4: t$_R$ 6.15 min, Purity 98%.

Example 3k (S,Z)-1-(biphenyl-4-ylmethyl)-3-(1-hydroxyethylidene)-5-isobutylpyrrolidine-2,4-dione (13k)

Synthesized according to the general procedure as described in Example 1b using (S)-methyl 2-(biphenyl-4-ylmethylamino)-4-methylpentanoate 11k of Example 2k (740 mg, 2.37 mmol), CH$_2$Cl$_2$ (20 mL), 50% diketene in CH$_2$Cl$_2$ (400 µL, 2.37 mmol) and Et$_3$N (five drops), to give amide (750 mg, 80%). To the solution of amide (440 mg, 1.11 mmol) in methanol (10 mL) was added Amberlyst A-26 resin (795 mg, 3.33 mmol) and the reaction was carried out as described in Example 1b to give 13k (240 mg, 60%). $^1$H NMR (500 MHz, CD$_3$OD): δ 0.82 (3H, d, J=6.59 Hz), 0.88 (3H, d, J=6.59 Hz), 1.66-1.76 (2H, m), 1.82 (1H, heptet), 2.49 (3H, s), 3.74-3.82 (1H, bs), 4.29 (1H, d, J=15.37), 5.13 (1H, d, J=15.1 Hz), 7.34 (1H, t, J=7.41 Hz), 7.39 (2H, d, J=7.96 Hz), 7.44 (2H, t, J=7.96 Hz), 7.62 (4H, t, J=8.23 Hz). ESI-MS: 362.1 (M−1). IR ν$_{max}$ (cm$^{-1}$): 2957, 1618 cm$^{-1}$. [α]$_D^{25.1}$− 53.5 (c=1%, CHCl$_3$). HPLC3: t$_R$ 3.15 min, Purity 98%. HPLC4: t$_R$ 6.85 min, Purity 98%.

Example 3l (5S,Z)-1-((6,6-dimethylbicyclo[3.1.1]hept-2-en-2-yl)methyl)-3-(1-hydroxyethylidene)-5-isobutylpyrrolidine-2,4-dione (13l)

Synthesized according to the general procedure as described in Example 1b using (2S)-methyl 2-((6,6-dimethylbicyclo[3.1.1]hept-2-en-2-yl)methylamino)-4-methylpentanoate 11l of Example 2l (920 mg, 3.29 mmol), CH$_2$Cl$_2$ (20 mL), 50% diketene in CH$_2$Cl$_2$ (554 µL, 3.29 mmol) and Et$_3$N (five drops) to give amide (970 mg, 81%). To the solution of amide (440 mg, 1.21 mmol) in methanol (10 mL) was added Amberlyst A-26 resin (864 mg, 3.63 mmol) and the reaction was carried out as described in Example 1b to give 13l (370 mg, 92%). $^1$H NMR (500 MHz, CD$_3$OD): δ 0.84 (1H, s), 0.88-0.93 (5H, m), 0.95 (3H, d, J=6.59 Hz), 1.12 (0.64, d, J=8.78 Hz), 1.2 (0.36H, d, J=8.54 Hz), 1.29 (1H, s), 1.32 (2H, s), 1.6-1.76 (2H, m), 1.89 (1H, sextet), 1.98-2.2 (0.64H, m), 2.1-2.14 (1.36H, m), 2.26-2.4 (2H, m), 2.4-2.5 (2H, m), 3.49 (0.66H, d, J=15.38 Hz), 3.59 (0.34H, d, J=15.62 Hz), 3.72-3.8 (0.65H, bs), 3.82-3.9 (0.35H, bs), 4.39 (0.34H, dd, J=1.95, 15.62 Hz), 4.5 (0.66H, dd, J=2.19, 15.13 Hz), 5.45 (0.35H, s), 5.55 (0.65H, s). ESI-MS: 330.1 (M−1). [α]$_D^{25.6}$−86.7 (c=1%, CHCl$_3$). HPLC3: t$_R$ 3.87 min, Purity 98%. HPLC4: t$_R$ 6.9 min, Purity 98%.

Example 3m (5S,Z)-1-(3,7-dimethyloct-6-enyl)-3-(1-hydroxyethylidene)-5-isobutylpyrrolidine-2,4-dione (13m)

Synthesized according to the general procedure as described in Example 1b using (2S)-methyl 2-(3,7-dimethyloct-6-enylamino)-4-methylpentanoate 11m of Example 2m (1.00 g, 3.52 mmol), CH$_2$Cl$_2$ (20 mL), 50% diketene in CH$_2$Cl$_2$ (593 µL, 3.52) and Et$_3$N (five drops) to give amide (800 mg, 62%). To the solution of amide (405 mg, 1.1 mmol) in methanol (10 mL) was added Amberlyst A-26 resin (787 mg, 3.3 mmol) and the reaction was carried out as described in Example 1b give 13m (290 mg, 78%). $^1$H NMR (500 MHz, CD$_3$OD): δ 0.91 (3H, d, J=6.34 Hz), 0.94-1.0 (6H, m), 1.14-1.3 (1H, m), 1.32-1.5 (3H, m), 1.56-1.76 (9H, m), 1.8-1.9 (1H, m), 1.98-2.1 (2H, m), 2.44 (3H, s), 3-3.12 (1H, m), 3.8-4.0 (2H, m), 5.1 (1H, q, J=6.83 Hz). ESI-MS: 334.1 (M−1). IR ν$_{max}$ (cm$^{-1}$): 2958, 2924, 1622 cm$^{-1}$. [α]$_D^{26.1}$− 34.9 (c=1%, CHCl$_3$). HPLC3: t$_R$ 4.22 min, Purity: 98%. HPLC4: t$_R$ 7.02 min, Purity 99%.

Example 3n (S,Z)-5-benzyl-1-decyl-3-(1-hydroxyethylidene)pyrrolidine-2,4-dione (13n)

Synthesized according to the general procedure as described in Example 1b using (S)-ethyl 2-(decylamino)-3-phenylpropanoate 11n of Example 2n (250 mg, 0.74 mmol), CH$_2$Cl$_2$ (10 mL), 50% diketene in CH$_2$Cl$_2$ (126 µL, 0.74 mmol) and Et$_3$N (five drops) to give amide (270 mg, 86%). To the solution of amide (230 mg, 0.55 mmol) in methanol (10 mL) was added Amberlyst A-26 resin (394 mg, 1.65 mmol) and the reaction was carried out as described in Example 1b to give 13n (150 mg, 74%). $^1$H NMR (500 MHz, CD$_3$OD): δ 0.92 (3H, d, J=7.07 Hz), 1.2-1.4 (14H, m), 1.46-1.62 (2H, m), 2.35 (3H, s), 3.04-3.14 (2H, m), 3.21-3.26 (1H, m), 3.78-3.86 (1H, m), 4.2-4.3 (1H, bs), 7.13-7.17 (2H, m), 7.18-7.28 (3H, m). ESI-MS: 370.1 (M−1). IR ν$_{max}$ (cm$^{-1}$): 2924, 1619 cm$^{-1}$. HPLC3: t$_R$ 4.59 min, Purity 95%. HPLC4: t$_R$ 7.22 min, Purity: 96%.

Example 3o (R,Z)-1-decyl-3-(1-hydroxyethylidene)-5-isobutylpyrrolidine-2,4-dione (13o)

Synthesized according to the general procedure as described in Example 1b using (R)-methyl 2-(decylamino)-4-methylpentanoate 11o of Example 2o (325 mg, 1.13 mmol), CH$_2$Cl$_2$ (10 mL), 50% diketene in CH$_2$Cl$_2$ (192 µL, 1.13 mmol) and Et$_3$N (five drops) to give amide (295 mg, 70%). To the solution of amide (270 mg, 0.73 mmol) in methanol (10 mL) was added Amberlyst A-26 resin (521 mg, 2.19 mmol) and the reaction was carried out as described in Example 1b to give 13o (180 mg 73%). $^1$H NMR (500 MHz, CDCl$_3$): δ 0.86-0.98 (9H, m), 1.2-1.36 (14H, m), 1.48-1.72 (4H, m), 1.86 (1H, heptet), 2.43 (2.52H, s, Me 3-acetyl major tautomer), 2.51 (0.48H, s, Me 3-acetyl minor tautomer), 2.9-3.02 (1H, m), 3.78 (1H, dd, J=4.15, 6.8 Hz), 3.82-3.9 (1H, m). ESI-MS: 336.1 (M−1). IR ν$_{max}$ (cm$^{-1}$):2 924, 1624 cm$^{-1}$. [α]$_D^{25.5}$−2.3 (c=1%, MeOH). HPLC3: t$_R$ 5.44 min, Purity 96%. HPLC4: t$_R$ 7.28 min, Purity 94%.

Example 4

General Procedure for Synthesis of Compounds of Formula II (N-Substituted 3-cyano Tetramic Acids)

N-substituted secondary amines described in Example 2 and shown in FIG. 2 were synthesized by reductive amination of amino acid ester salts with various alkyl and aryl aldehydes using sodium borohydride as a reducing agent. The secondary amines 11a-g and 11p were converted into respective cyano amides by reacting with cyano acetic acid. Cyano amides were subsequently cyclized into tetramic acids by treating with Amberlyst A-26 hydroxide resin.

Example 4a

General Procedure for Synthesis of Secondary Amines

Secondary amines were made as described in Example 1a.

Example 4b

General Procedure for Synthesis of N-Substituted 3-cyano Tetramic Acids

To a solution of substituted amino acids (1 equiv) in CH$_2$Cl$_2$ was added cyanoacetic acid (1.12 equiv), HOBt (1.12 equiv), and either DIC or DCC (1.4 equiv) and stirred for 6 h at rt. The reaction mixture was subsequently filtered, diluted with CH$_2$Cl$_2$ and washed with water, saturated NaHCO$_3$ and brine. The organic fraction was dried over Na$_2$SO$_4$ and concentrated. This was purified by flash column chromatography using a petroleum ether to ethyl acetate gradient elution to afford amides. To the solution of amide (1 equiv) in methanol (10 mL) was added Amberlyst A-26 resin (4.2 meq/gm, 3 equiv) and the reaction was stirred at rt under argon for 2 h. Resin containing the product was filtered and washed with methanol (3×10 mL). The resin was then stirred for 30 min with methanol (10 mL) and TFA (400 μL), filtered and washed with methanol (3×10 mL). Concentration of the eluent afforded the desired products.

Example 5

Synthesis of N-Substituted 3-cyano Tetramic Acids

Figure 5:
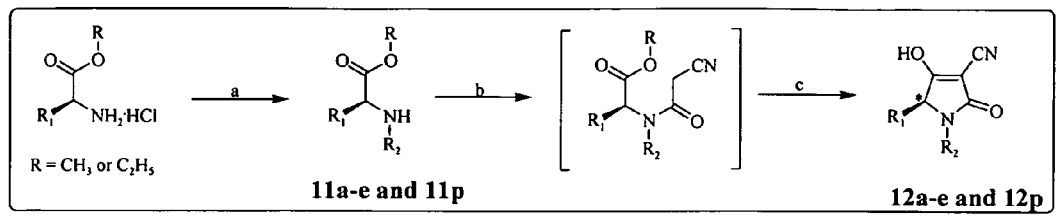
FIG. 5 shows the synthetic scheme for making N-substituted 3-cyano tetramic acid derivatives from amino acid ester salts. (A) shows synthesis starting with L-amino acid ester salts. (B) shows synthesis starting with D-amino acid ester salts. Reagents and conditions for the synthetic schemes were as follows: (a) (i) Aldehydes, $Et_3N$, $MgSO_4$, THF, room temperature, 5 hours; (ii) $NaBH_4$, MeOH, room temperature, 30 minutes; (b) Cyanoacetic acid, HOBt, DIC, or DCC, $CH_2Cl_2$, room temperature, 6 hours (c) (i) Amberlyst A-26 hydroxide resin, MeOH, room temperature, 2 hours, (ii) MeOH, TFA, room temperature, 20 minutes. * Indicates racemizations might have occurred during synthesis.
Figure 5:
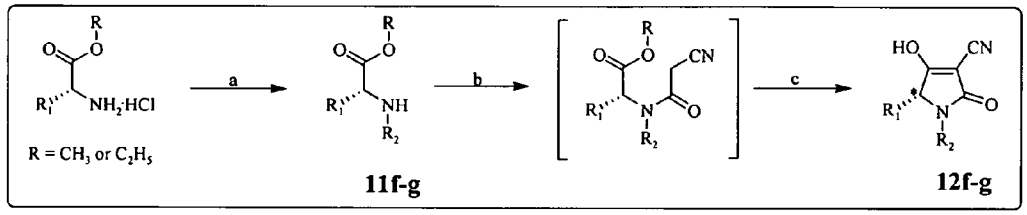
Figure 6:
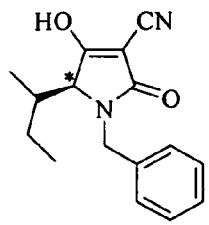
FIG. 6 shows the chemical structure of compounds of Formula II designated 12a to 12g and 12p, as follows. 12a is (S)-1-benzyl-5-sec-butyl-4-hydroxy-2-oxo-2,5-dihydro-1H-pyrrole-3-carbonitrile. 12b is (S)-1-decyl-4-hydroxy-5-isobutyl-2-oxo-2,5-dihydro-1H-pyrrole-3-carbonitrile. 12c is (S)-1,5-dibenzyl-4-hydroxy-2-oxo-2,5-dihydro-1H-pyrrole-3-carbonitrile. 12d is (S)-4-hydroxy-5-isobutyl-1-(3-methoxybenzyl)-2-oxo-2,5-dihydro-1H-pyrrole-3-carbonitrile. 12e is (S)-1-(4-fluorobenzyl)-4-hydroxy-5-isobutyl-2-oxo-2,5-dihydro-1H-pyrrole-3-carbonitrile. 12f is (R)-1-(4-fluorobenzyl)-4-hydroxy-5-isobutyl-2-oxo-2,5-dihydro-1H-pyrrole-3-carbonitrile. 12g is (R)-1,5-dibenzyl-4-hydroxy-2- oxo-2,5-dihydro-1H-pyrrole-3-carbonitrile. 12p is (S)-5-sec-butyl-1-(furan-2-ylmethyl)-4-hydroxy-2-oxo-2,5-dihydro-1H-pyrrole-3-carbonitrile.
Figure 6:
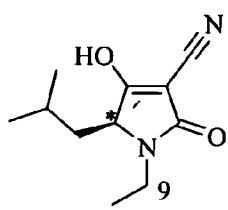
Figure 6:
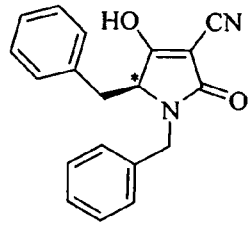
Figure 6:
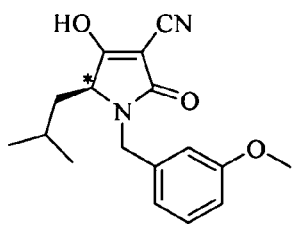
Figure 6:
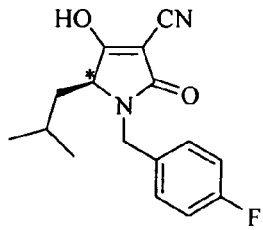
Figure 6:
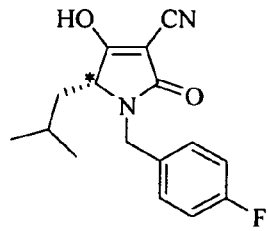
Figure 6:
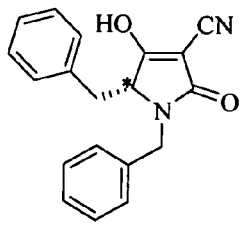
Figure 6:
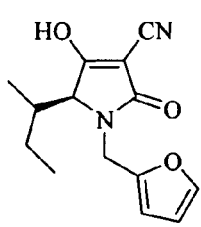

N-substituted 3-cyano tetramic acids were synthesized by the scheme shown in FIGS. 5a and 5b, utilizing the secondary amines of FIG. 2 as starting material. The respective N-substituted 3-acyl cyano tetramic acids were designated 12a to 12g and 12p, respectively, the structures of which are shown in FIG. 6.

Example 5a (S)-1-benzyl-5-sec-butyl-4-hydroxy-2-oxo-2,5-dihydro-1H-pyrrole-3-carbonitrile (12a)

Synthesized according to the general procedure as described in Example 4b using (2S,3S)-methyl 2-(benzylamino)-3-methylpentanoate 11a of Example 2a (880 mg, 3.74 mmol), $CH_2Cl_2$ (20 mL), cyanoacetic acid (358 mg, 4.19 mmol), HOBt (566 mg, 4.19 mmol), DCC (1.08 gm, 5.23 mmol) to give amide (650 mg, 57%). To the solution of amide (180 mg, 0.596 mmol) in methanol (10 mL) was added Amberlyst A-26 resin (425 mg, 1.78 mmol) and the reaction was carried out as described in Example 4b to give 12a (140 mg, 87%). $^1$H NMR (500 MHz, $CD_3OD$): δ 0.78 (3H, d, J=6.86 Hz), 0.88 (3H, d, J=7.96 Hz), 1.42-1.6 (2H, m), 1.9-2.08 (1H, m), 3.94 (1H, d, J=3.02 Hz), 4.18 (1H, d, J=15.37 Hz), 5.01 (1H, d, J=15.37 Hz), 7.27 (2H, d, J=6.86 Hz), 7.72-7.33 (1H, m), 7.34-7.39 (2H, m). ESI-MS: 268.9 (M−1). IR $\nu_{max}$ ($cm^{-1}$): 2225.86, 1642.35, 1570.15 $cm^{-1}$. $[\alpha]_D^{26.2}$−62.2 (c=1%, MeOH). HPLC1: $t_R$ 5.87 min, Purity >99%. HPLC2: $t_R$ 5.11 min, Purity 98%.

Example 5b (S)-1-decyl-4-hydroxy-5-isobutyl-2-oxo-2,5-dihydro-1H-pyrrole-3-carbonitrile (12b)

Synthesized according to the general procedure as described in Example 4b using (S)-methyl 2-(decylamino)-4-methylpentanoate 11b of Example 2b (135 mg, 0.47 mmol), $CH_2Cl_2$ (5 mL), cyanoacetic acid (45 mg, 0.53 mmol), HOBt (72 mg, 0.53 mmol), and DCC (137 mg, 0.66 mmol) to give amide (74 mg, 44%). To the solution of amide (74 mg, 0.21 mmol) in methanol (5 mL) was added Amberlyst A-26 resin (150 mg, 0.63 mmol) and the reaction was carried out as described in Example 4b to give 12b (40 mg, 59%). $^1$H NMR (500 MHz, $CDCl_3$): δ 0.90 (3H, t, J=7.07 Hz), 0.93 (3H, d, J=6.83 Hz), 0.96 (3H, d, J=6.59 Hz), 1.24-1.36 (14H, m), 1.48-1.6 (2H, m), 1.62-1.76 (2H, m), 1.95 (1H, heptet), 2.96-3.06 (1H, m), 3.68-3.8 (1H, m), 4.08-4.14 (1H, m). ESI-MS: 319.1 (M−1). IR $\nu_{max}$ ($cm^{-1}$): 2924.91, 2227.97, 1634.87 $cm^{-1}$. $[\alpha]_D^{27.6}$+0.6 (c=1%, MeOH). HPLC1 $t_R$ 7.7 min, Purity >99%. HPLC2: $t_R$ 6.5 min, Purity 97%.

Example 5c (S)-1,5-dibenzyl-4-hydroxy-2-oxo-2,5-dihydro-1H-pyrrole-3-carbonitrile (12c)

Synthesized according to the general procedure as described in Example 4b using (S)-ethyl 2-(benzylamino)-3-phenylpropanoate 11c of Example 2c (500 mg, 1.76 mmol), $CH_2Cl_2$ (15 mL), cyanoacetic acid (168 mg, 1.97 mmol), HOBt (268 mg, 1.97 mmol), and DCC (510 mg, 2.47 mmol) to give amide (350 mg, 57%). To the solution of amide (350 mg, 0.998 mmol) in methanol (10 mL) was added Amberlyst A-26 resin (713 mg, 2.99 mmol) and the reaction was carried out as described in Example 4b to give 12c (270 mg, 89%). $^1$H NMR (500 MHz, $CD_3OD$): δ 3.05 (1H, dd, J=4.94, 14.55 Hz), 3.29 (1H, d, J=4.39 Hz), 4.1-4.2 (2H, m), 5.08 (1H, d, J=15.37 Hz), 7.12-7.2 (4H, m), 7.26-7.32 (4H, m), 7.33-7.37 (2H, m). ESI-MS: 302.9 (M−1). IR $\nu_{max}$ ($cm^{-1}$): 2221.9, 1595 $cm^{-1}$. $[\alpha]_D^{28}$−86.4 (c=1%, MeOH). HPLC1: $t_R$ 5.95 min, Purity >99%. HPLC2: $t_R$ 5.2 min, Purity 98%.

Example 5d (S)-4-hydroxy-5-isobutyl-1-(3-methoxybenzyl)-2-oxo-2,5-dihydro-1H-pyrrole-3-carbonitrile (12d)

Synthesized according to the general procedure as described in Example 4b using (S)-methyl 2-(3-methoxybenzylamino)-4-methylpentanoate 11d of Example 2d (510 mg, 1.92 mmol), $CH_2Cl_2$ (20 mL), cyanoacetic acid (183 mg, 2.15 mmol), HOBt (291 mg, 2.15 mmol), and DIC (416 μL, 2.68 mmol) to give amide (520 mg, 81%). To the solution of amide (520 mg, 1.564 mmol) in methanol (10 mL) was added Amberlyst A-26 resin (1.11 gm, 4.69 mmol) and the reaction was carried out as described in Example 4b to give 12d (260 mg, 55%). $^1$H NMR (500 MHz, DMSO-$d_6$): δ 0.75 (6H, t, J=5.85 Hz), 1.54-1.64 (3H, m), 3.73 (3H, s), 3.76-3.82 (1H, m), 4.09 (1H, d, J=15.62 Hz), 4.75 (1H, d, J=15.62 Hz), 6.76-6.8 (2H, m), 6.82-6.85 (1H, m), 7.24 (1H, t, J=8.05 Hz). ESI-MS: 299.1 (M−1). IR $\nu_{max}$ ($cm^{-1}$): 2227.04, 1586.44 $cm^{-1}$. $[\alpha]_D^{28}$−3.9 (c=1%, MeOH). HPLC1: $t_R$ 5.82 min, Purity >99%. HPLC2: $t_R$ 5.11 min, Purity 93%.

Example 5e (S)-1-(4-fluorobenzyl)-4-hydroxy-5-isobutyl-2-oxo-2,5-dihydro-1H-pyrrole-3-carbonitrile (12e)

Synthesized according to the general procedure as described in Example 4b using (S)-methyl 2-(4-fluorobenzylamino)-4-methylpentanoate 11e of Example 2e (510 mg, 2.01 mmol), $CH_2Cl_2$ (20 mL), cyanoacetic acid (192 mg, 2.25 mmol), HOBt (304 mg, 2.25 mmol), and DIC (435 μL, 2.81 mmol) to give amide (450 mg, 70%). To the solution of amide (210 mg, 0.655 mmol) in methanol (10 mL), was added Amberlyst A-26 resin (466 mg, 1.96 mmol) and the reaction was carried out as described in Example 4b to give 12e (140 mg, 74%). $^1$H NMR (500 MHz, $CDCl_3$): δ 0.82 (3H, d, J=6.34 Hz), 0.85 (3H, d, J=6.59 Hz), 1.6-1.72 (2H, m), 1.84 (1H, heptet), 3.88-3.93 (1H, m), 4.02-4.1 (1H, m), 5.02-5.12 (1H, m), 6.99 (2H, t, J=8.54 Hz), 7.21 (2H, dd, J=5.12, 8.54 Hz). ESI-MS: 287 (M−1). IR $\nu_{max}$ ($cm^{-1}$): 2227.18, 1642.93 $cm^{-1}$. $[\alpha]_D^{28}$−8.5 (c=1%, MeOH). HPLC1: $t_R$ 5.99 min, Purity >99%. HPLC2: $t_R$ 5.19 min, Purity 98%.

Example 5f

(R)-1-(4-fluorobenzyl)-4-hydroxy-5-isobutyl-2-oxo-2,5-dihydro-1H-pyrrole-3-carbonitrile (12f)

Synthesized according to the above general pr to the general procedure as described in Example 4b using (R)-methyl 2-(4-fluorobenzylamino)-4-methylpentanoate 11f of Example 2f (510 mg, 2.01 mmol), $CH_2Cl_2$ (20 mL), cyanoacetic acid (192 mg, 2.25 mmol), HOBt (304 mg, 2.25 mmol), and DIC (435 μL, 2.81 mmol) to give amide (365 mg, 57%). To the solution of amide (360 mg, 1.12 mmol) in methanol (10 mL) was added Amberlyst A-26 resin (802 mg, 3.37 mmol) and the reaction was carried out as described in Example 4b to give 12f (240 mg, 74%). $^1$H NMR (500 MHz, $CDCl_3$): δ 0.82 (3H, d, J=6.59 Hz), 0.84-0.87 (3H, m), 1.59-1.72 (2H, m), 1.86 (1H, heptet), 3.88-3.94 (1H, m), 4.04-4.14 (1H, m), 5.02-5.12 (1H, m), 6.99 (2H, t, J=8.51 Hz), 7.22 (2H, dd, J=5.21, 8.54 Hz). ESI-MS: 287 (M−1). IR $v_{max}$ ($cm^{-1}$): 2227.61, 1642.63 $cm^{-1}$. $[\alpha]_D^{25.6}$+20.5 (c=1%, MeOH). HPLC1: $t_R$ 6.09 min, Purity 92%. HPLC2: $t_R$ 5.22 min, Purity 97%.

Example 5g

(R)-1,5-dibenzyl-4-hydroxy-2-oxo-2,5-dihydro-1H-pyrrole-3-carbonitrile (12g)

Synthesized according to the general procedure as described in Example 4b using (R)-methyl 2-(benzylamino)-3-phenylpropanoate 11g of Example 2g (600 mg, 2.23 mmol) in $CH_2Cl_2$ (15 mL), cyanoacetic acid (212 mg, 2.49 mmol), HOBt (336 mg, 2.49 mmol), and DCC (644 mg, 3.12 mmol) to give amide (515 mg, 68%). To the solution of amide (510 mg, 1.517 mmol) in methanol (10 mL) was added Amberlyst A-26 resin (1.083 g, 4.55 mmol) and the reaction was carried out as described in Example 4b to give 12g (320 mg, 70%). $^1$H NMR (500 MHz, DMSO-$d_6$): δ 2.92 (1H, dd, J=4.66, 14.28 Hz), 3.13 (1H, dd, J=4.39, 14.28 Hz), 3.84 (1H, t, J=4.66 Hz), 3.97 (1H, d, J=15.37 Hz), 4.86 (1H, d, J=15.1 Hz), 7.08 (4H, d, J=6.86 Hz), 7.17-7.27 (4H, m), 7.28-7.33 (2H, m). ESI-MS: 303 (M−1). IR $v_{max}$ ($cm^{-1}$): 1595.66, 2222.02 $cm^{-1}$. $[\alpha]_D^{27}$+83.0 (c=1%, MeOH). HPLC1: $t_R$ 5.87 min, Purity 97%. HPLC2: $t_R$ 5.3 min, Purity >99%.

Example 5h

(S)-5-sec-butyl-1-(furan-2-ylmethyl)-4-hydroxy-2-oxo-2,5-dihydro-1H-pyrrole-3-carbonitrile (12p)

Synthesized according to the general procedure as described in Example 4b using (2S,3S)-methyl 2-(furan-2-ylmethylamino)-3-methylpentanoate 11p of Example 2p (422 mg) in $CH_2Cl_2$ (20 mL), cyanoacetic acid (179 mg), HOBt (283 mg) and DCC (540 mg) to give amide (320 mg, 58%). To the solution of amide (300 mg) in methanol (10 mL) was added Amberlyst A-26 resin (734 mg) and the reaction was carried out as described in Example 4b to give 12p (160 mg, 60%). $^1$H NMR (500 MHz, $CDCl_3$): δ 0.82 (3H, d, J=7.14 Hz), 0.96 (3H, t, J=7.41 Hz), 1.5-1.66 (2H, m), 2.04-2.12 (1H, m), 4.04 (1H, d, J=3.02 Hz), 4.13 (1H, d, J=15.65 Hz), 5.03 (1H, d, J=15.65 Hz), 6.29 (1H, d, J=3.02 Hz), 6.34 (1H, t, J=1.92 Hz), 7.37 (1H, d, J=1.37 Hz). ESI-MS: 259 (M−1). IR $v_{max}$ ($cm^{-1}$): 2225.49, 1641.26, 1567.22 $cm^{-1}$. $[\alpha]_D^{27.7}$−21.5 (c=1%, MeOH). HPLC1: $t_R$ 5.87 min, Purity: 96%. HPLC2: $t_R$ 4.88 min, Purity: 92%.

Example 6

Antibacterial Activity Assays

Cultures of *Mycobacterium tuberculosis, Escherichia coli, Staphylococcus aureus, Enterococcus faecalis, Bacillus anthracis, Bacillus subtilis, Pseudomonas aeruginosa, Streptococcus pyogenes, Propionibacterium acnes*, and *Streptococcus pneumoniae* were grown to mid-log in 7H9 broth containing albumin-dextrose complex (ADC). Mueller-Hinton or Brain Heart Infusion broth then stored for future use at −80° C. Drug compounds of Formula I of Example 3 and drug compounds of Formula II of Example 5 were diluted to a concentration of 10 mg/mL in DMSO and stored for use at −80° C. Two fold serial dilutions of the drug in media were prepared in 96-well plates starting at a concentration of 200 μg/ml and ending at a concentration of 0.1 μg/ml. Thawed stock cultures were streaked onto Mueller-Hinton agar and incubated at a temperature of 37° C. over a 16 hour period. Subsequently, colonies were picked from the plates and used to prepare cultures in broth at an inocula OD of $\lambda_{600}$=0.001. One hundred μl of these cultures were added to each well of the 96-well plates resulting in an OD of 400=0.0005, which correspond to about $10^5$ CFU/ml. The 96-well plates were incubated overnight at 37° C. *Mycobacterium tuberculosis* H37Rv was tested in 7H9 broth complex with incubation for 7 days at 37° C. The Minimum Inhibitory Concentration (MIC) was recorded as the lowest concentration which prevented visible growth of bacteria and provides a measure of the potency of antibacterial compounds.

Example 7

Cytotoxicity Assays

Cytotoxicity assays of drugs of Formula I of Example 3 and of Formula II of Example 5 were performed using the Vero monkey kidney cell line (ATCC, CCL-81). Vero cells were grown in tissue culture flasks in Dulbecco's Modified Eagle's Medium (ATCC) supplemented with 10% fetal bovine serum and maintained in a humidified incubator (37° C., 5% $CO_2$). Cells were removed with a cell scraper, collected by centrifugation and then suspended in fresh medium at ~$10^6$ cells/mL. The cell suspensions were dispensed into 96-well microtiter plates (100 μl/well) and incubated for 18 hours at 37° C. before being used for cytotoxicity assays. Test compounds were subsequently added at concentrations ranging from 400-0.024 μg/mL and 0.1% vol/vol of Triton-X 100, which causes 100% death of cells, was included as a control. After incubating cells and compounds for 72 hours in humid air (37° C., 5% $CO_2$) the cytopathic effects of compounds were determined using the MTT Cell Proliferation Assay (ATCC, Cat No. 30-1010K). The MTT solution reagent (10 μl) was added to each well and plates incubated at 37° C. until sufficient purple color development occurred in cells (3 hours). After detergent cell lysis, the purple formazan product was measured at 570 nm in a Synergy HT Biotek microplate reader. $IC_{50}$ data was obtained from dose response curves plotted from percentage activity versus $\log_{10}$ concentration using Graphpad prism 5.

Example 8

Results of Antibacterial Activity and Cytotoxicity Assays

The results of the studies of Examples 6 and 7 are shown in Table I.

TABLE 1

| Compound | Activity µg/mL | | | | | | | | | $IC_{50}$ | $IC_{50}$/MIC |
|---|---|---|---|---|---|---|---|---|---|---|---|
| | TB | BA | BS | SPn | EF | MRSA | MSSA | PA | SP | | |
| 12a | >200 | >200 | >200 | >200 | >200 | >200 | >200 | >200 | >200 | NA | NA |
| 12b | 3.12 | 25 | 50 | 100 | 25 | 25 | 25 | 12.5 | >200 | 152.4 | 6.1 |
| 12c | >200 | >200 | >200 | >200 | >200 | >200 | >200 | >200 | >200 | NA | NA |
| 12d | >200 | >200 | >200 | >200 | >200 | >200 | >200 | >200 | >200 | NA | NA |
| 12e | >200 | >200 | >200 | >200 | >200 | >200 | >200 | >200 | >200 | NA | NA |
| 12f | >200 | >200 | >200 | >200 | >200 | >200 | >200 | >200 | >200 | NA | NA |
| 12g | >200 | >200 | >200 | >200 | >200 | >200 | >200 | >200 | >200 | NA | NA |
| 12p | >200 | 3.12 | 25 | 50 | 3.12 | >200 | >200 | 12.5 | >200 | 6395 | 2049.7 |
| 13a | 50 | 3.12 | 25 | 50 | 6.25 | 6.25 | 6.25 | 6.25 | >200 | 26.3 | 4.2 |
| 13b | 12.5 | 0.8 | 0.8 | 6.25 | 1.6 | 0.8 | 0.4 | 0.8 | 50 | 14.7 | 36.8 |
| 13c | >200 | 25 | 25 | 100 | 100 | 25 | 12.5 | 12.5 | >200 | 75.7 | 6.1 |
| 13d | 100 | 25 | 25 | 50 | 100 | 25 | 12.5 | 12.5 | 200 | 40.0 | 3.2 |
| 13e | 100 | 12.5 | 25 | 50 | 50 | 25 | 12.5 | 6.25 | 100 | 27.8 | 2.2 |
| 13f | 100 | 12.5 | 12.5 | 25 | 50 | 12.5 | 12.5 | 12.5 | 100 | 35.3 | 2.8 |
| 13g | >200 | 25 | 25 | 50 | 100 | 25 | 25 | 25 | 200 | 80.6 | 3.2 |
| 13h | >200 | 50 | >200 | >200 | >200 | >200 | 200 | 100 | >200 | NA | NA |
| 13i | 12.5 | 0.8 | 0.4 | 6.25 | 0.8 | 0.8 | 0.8 | 0.4 | 25 | 7.0 | 8.8 |
| 13j | 100 | 12.5 | 6.25 | 100 | 1.6 | 6.25 | 3.12 | 0.8 | >200 | 254.0 | 81.4 |
| 13k | 50 | 0.4 | 0.4 | 12.5 | 0.8 | 0.8 | <0.1 | 0.2 | 25 | 19.7 | >197 |
| 13l | 100 | 0.8 | 1.6 | 50 | 1.6 | 1.6 | 1.6 | 0.8 | 25 | 35.4 | 22.1 |
| 13m | 200 | 0.4 | 0.8 | 3.25 | 0.8 | 0.8 | 0.4 | 0.4 | 25 | 7.3 | 18.3 |
| 13n | 50 | 0.2 | 0.4 | 12.5 | 0.8 | 0.8 | 0.2 | 0.4 | 50 | 21.1 | 105.5 |
| 13o | 25 | 0.8 | 0.8 | 6.25 | 1.6 | 0.8 | 0.4 | 0.8 | 50 | 6.3 | 15.8 |

TB: *Mycobacterium tuberculosis* H37 Rv;
BA: *Bacillus anthracis* Sterne 34F2;
BS: *Bacillus subtilis* ATCC 23857;
SPn: *Streptococcus pneumoniae* DAW30EC;
EF: *Enterococcus faecalis* ATCC 33186;
MRSA: Methicillin Resistant *Staphylococcus aureus* ATCC 33591;
MSSA: Methicillin sensitive *Staphylococcus aureus* 8325 ATCC 35556;
PA *Propionibacterium acnes* ATCC 6919;
SP: *Streptococcus pyogenes* ATCC 700294;
$IC_{50}$ (Cytotoxicity): Concentration which reduces viability of Vero kidney cells by 50%;
$IC_{50}$/MIC = Selectivity (therapeutic) index: $IC_{50}$ divided by MIC against *S. aureus* 8325, except for 12p, $IC_{50}$ divided by MIC against *E. faecalis*;
NA: Not Assessed.

As shown in Table 1, the compounds of Formula I (13a to 13o) and of Formula II (12a to 12g, and 12p) are primarily effective against gram-positive organisms. Compound 12b, an N-substituted 3-cyano tetramic acid derivative, was the most active compound against *M. tuberculosis* (MIC of 3.12 µg/mL) of all compounds tested. N-substituted 3-acyl tetramic acids (13a-o) exhibited good activity against a wide range of bacterial strains. In the Formula I class of compounds, compounds 13b and 13i were the most active compounds against tuberculosis. It appears that $R_1$ substitutions at 5-position does not seem to play a major role in determining antibacterial activity as 13b, 13i and 13n have similar activities.

From the MIC activity values it is clear that stereochemistry does not play a role in determining the activity. In N-substituted 3-cyano tetramic acids Formula II series, the compounds synthesized from D-amino acids ester salts 12f and 12g and their corresponding analogs that were synthesized from L-amino acid ester salts 12e and 12c did not exhibit any antibacterial properties. In N-substituted 3-acyl tetramic acids the compounds that were synthesized from D-amino acids ester salts 13f, 13g and 13o and their corresponding analogs that were synthesized from L-amino acid ester salts 13e, 13c and 13b have similar activities.

The majority of the compounds demonstrating good antimicrobial activity also exhibited a favorable therapeutic index (>10) appropriate for clinical application. The data shows that there is a general selectivity for inhibition of bacterial cells compared to mammalian counterpart cells.

Example 9

Activity of Tetramic Acid Analogues Against Clinical Isolates

Several tetramic acid analogues of Formula I (13b, 13j, 13k, 13l, and 13n) were tested against clinical isolates of MRSA (methicillin resistant *S. aureus*) and MSSA (methicillin sensitive *S. aureus*). The isolates were obtained from Le Bonheur Children's Medical Center, Memphis, Tenn. Results are shown below in Table 2.

TABLE 2

| ISOLATE | Antibiotic MIC µg/mL | | | | |
|---|---|---|---|---|---|
| | 13b | 13j | 13k | 13l | 13n |
| MRSA-1 | 0.8 | 50 | 1.6 | 3.12 | 1.6 |
| MRSA-2 | 0.8 | 25 | 1.6 | 3.12 | 1.6 |
| MRSA-3 | 0.8 | 25 | 1.6 | 3.12 | 1.6 |
| MRSA-4 | 0.8 | 25 | 1.6 | 3.12 | 0.8 |
| MRSA-5 | 0.8 | 25 | 1.6 | 3.12 | 0.8 |
| MRSA-6 | 1.6 | 25 | 0.8 | 3.12 | 0.8 |
| MRSA-7 | 0.8 | 50 | 0.8 | 3.12 | 0.8 |
| MRSA-8 | 0.4 | NT | 0.4 | 0.4 | 0.2 |
| MRSA-9 | 0.8 | 6.25 | 1.6 | 3.12 | 0.8 |
| MRSA-10 | 0.8 | 50 | 0.8 | 3.12 | 0.8 |
| MSSA-11 | 0.8 | 12.5 | 1.6 | 3.2 | 0.8 |
| MSSA-12 | 0.4 | 6.25 | 0.8 | 1.6 | 0.8 |
| MSSA-13 | 0.4 | 12.5 | 0.8 | 1.6 | 0.8 |
| MSSA-14 | 0.4 | 25 | 0.8 | 3.2 | 1.6 |
| MSSA-15 | 0.4 | 3.12 | 0.4 | 1.6 | 0.2 |
| MSSA-16 | 0.4 | 6.25 | 0.8 | 1.6 | 0.8 |
| MSSA-17 | 0.4 | 6.25 | 0.8 | 1.6 | 0.8 |
| MSSA-18 | 0.4 | 6.25 | 0.8 | 1.6 | 0.8 |
| MSSA-19 | 0.4 | 3.12 | 0.8 | 1.6 | 0.4 |
| MSSA-20 | 0.8 | 25 | 0.8 | 1.6 | 0.8 |

As shown in Table 2, all compounds of the invention tested were efficacious against clinical isolates of both methicillin resistant and methicillin sensitive *S. aureus*. Compounds 13b and 13n showed the highest efficacy against most of the isolates.

Example 10

Activity of Tetramic Acid Analogues Against Biofilms

Utilizing standard procedures for the 96-well Calgary Biofilm Device, disclosed in Ceri, et al, "The Calgary Biofilm Device: new technology for rapid determination of antibiotic susceptibilities of bacterial biofilms," Journal of Clinical Microbiology, 37(6):1771-1776 (1999), the ability of tetramic acid analogues of the invention to eradicate biofilms was tested. The biofilms tested were formed by staphylococcal bacteria, MRSA (ATCC 35391), MSSA (ATCC 25293), and *S. epidermidis* (RP62A). The ability of the compounds of the invention to eradicate the biofilms was compared with rifampicin, a positive control antibiotic known to be effective against biofilms, and vancomycin, a negative control antibiotic that is not effective against biofilms. Additional antibiotics tested were mupirocin and ciprofloxacin. Tests were run in triplicate. The results are shown in Table 3.

TABLE 3

| ANTIBIOTIC | ANTI-BIOFILM ACTIVITY µg/mL | | | | | |
|---|---|---|---|---|---|---|
| | MRSA | | S. epidermidis | | MSSA | |
| | MBIC | MBEC | MBIC | MBEC | MBIC | MBEC |
| 13b | 0.8 | 6.25 | 0.4 | 50 | 0.8 | 100 |
| 13b | 0.8 | 6.25 | 0.4 | 50 | 0.8 | 100 |
| 13b | 0.8 | 12.5 | 0.4 | 50 | 0.8 | 100 |
| 13i | 0.8 | 25 | 0.8 | 50 | 0.8 | 100 |
| 13i | 0.8 | 25 | 0.8 | 25 | 0.8 | 100 |
| 13i | 0.8 | 25 | 0.8 | 50 | 0.8 | 100 |
| 13k | 0.8 | 100 | 1.6 | 200 | 3.12 | 100 |
| 13k | 0.8 | 100 | 1.6 | 200 | 3.12 | 100 |
| 13k | 0.8 | 100 | 1.6 | 100 | 3.12 | 100 |
| 13l | 1.6 | >400 | 1.6 | >400 | 3.12 | >400 |
| 13l | 1.6 | >400 | 1.6 | >400 | 3.12 | >400 |
| 13l | 1.6 | >400 | 1.6 | >400 | 3.12 | >400 |

TABLE 3-continued

| ANTIBIOTIC | ANTI-BIOFILM ACTIVITY µg/mL | | | | | |
|---|---|---|---|---|---|---|
| | MRSA | | S. epidermidis | | MSSA | |
| | MBIC | MBEC | MBIC | MBEC | MBIC | MBEC |
| 13m | 0.8 | 50 | 0.4 | 200 | 0.8 | 200 |
| 13m | 0.8 | 50 | 0.8 | 200 | 0.8 | 200 |
| 13m | 0.4 | 50 | 0.8 | 100 | 1.6 | 100 |
| Rifampicin | <0.2 | 12.5 | <0.2 | 100 | 0.4 | 100 |
| Rifampicin | <0.2 | 12.5 | <0.2 | 200 | <0.2 | 100 |
| Rifampicin | <0.2 | 6.25 | <0.2 | 50 | <0.2 | 200 |
| Vancomycin | 1.6 | >400 | 12.5 | >400 | 12.5 | >400 |
| Vancomycin | 1.6 | >400 | 12.5 | >400 | 6.12 | >400 |
| Vancomycin | 1.6 | >400 | 12.5 | >400 | 12.5 | >400 |
| Mupirocin | <0.2 | >400 | <0.2 | >400 | <0.2 | >400 |
| Mupirocin | <0.2 | >400 | <0.2 | >400 | <0.2 | >400 |
| Mupirocin | <0.2 | >400 | <0.2 | >400 | <0.2 | >400 |
| Ciprofloxacin | <0.2 | 100 | <0.2 | 200 | 0.4 | >400 |
| Ciprofloxacin | <0.2 | >400 | <0.2 | 400 | 0.4 | >400 |
| Ciprofloxacin | <0.2 | 12.5 | <0.2 | 400 | 0.4 | >400 |

MBIC = Minimum Biofilm Inhibitory Concentration
MBEC = Minimum Biofilm Eradication Concentration As shown in Table 3, the tetramic acid analogues of the invention exhibited good activity against biofilms, comparable to rifampicin and superior to mupirocin, vancomycin, and ciprofloxacin. Whereas MBIC indicates the inhibitory activity of drug against cells dispersed from a biofilm, but retaining some biofilm characteristics, MBEC indicates whether drug can completely eradicate biofilm cells. Even though an antibiotic may have activity against dispersed cells, as indicated by an MBIC of 200 or less, the antibiotic may not be active against biofilms, as indicated by an MBEC greater than 200.

Table 3 shows that, although vancomycin, ciprofloxacin, and mupirocin had a low MBIC, and thus were active against dispersed bacteria, these antibiotics did not eradicate the biofilms, as shown by MBECs generally above >400 µg/mL. Four of the five compounds of the invention were shown to eradicate the biofilms at concentrations 6.25-200 µg/mL, similar to the positive control antibiotic rifampicin. An important advantage of the compounds of the invention compared to rifampicin is that resistance to rifampicin readily emerges in *Staphylococcus aureus*. In contrast, from a population of $10^{10}$ cells single-step mutants resistant to compound 13b of the invention could not be obtained.

Example 11

Efficacy of Tetramic Acid Analogs in Treating Infections of Skin

Compounds of the invention were tested for the ability to treat skin infections utilizing an established animal model of skin infection. The superficial skin infection model used in this study was previously developed by Kugelberg et al, "Establishment of a Superficial Skin Infection Model in Mice using *Staphylococcus aureus* and *Streptococcus pyogenes*", Antimicrob. Agents Chemother., 49(8):3435-3441 (2005).

Superficial infections in Balb/c mice (male) were caused by first removing hair from the backs of mice with an electric shaver, followed by dry shaving with a razor and tape stripping with Tensoplast® (BSN Medical Inc., Charlotte, N.C.) adhesive bandage to remove the epidermis, followed by infection with a 5 µl bacterial suspension containing about $10^7$ bacterial cells of methicillin-sensitive *S. aureus* ATCC 29213, a strain from a previous isolate from a human wound infection and used in other murine infection studies. After 4 hours of infection, treatment was started by administering 45-50 mg of ointment containing (i) vehicle hydrophilic petrolatum (placebo) (ii) 2% w/w mupirocin ointment (Bactroban®, GlaxoSmithKline plc., United Kingdom) in vehicle or (iii) 2% tetramic acid analogue of the invention (13b) in vehicle, (iv) 10% tetramic acid analogue of the invention (13b) in vehicle, (v) 2% tetramic acid analogue of the invention (13l) in vehicle, or (vi) 10% tetramic acid analogue of the invention (13l) in vehicle. Treatment was continued for three days with drug application twice daily at 8 hour intervals. On day 5, mice were sacrificed and the numbers of bacteria in lesions were enumerated. Results are shown in Table 4.

TABLE 4

| Treatment Group | Mean Bacterial Count ($\log_{10}$) +/− SD |
|---|---|
| Placebo | 8.15 +/− 0.37 |
| Mupirocin 2% | 5.95 +/− 0.92 |
| 13b 2% | 8.08 +/− 0.28 |
| 13b 10% | 6.47 +/− 0.58 |
| 13l 2% | 7.67 +/− 0.21 |
| 13l 10% | 6.51 +/− 0.67 |

Results shown in Table 4 establish that, at 10% concentration, the compounds of the invention significantly reduced the number of bacteria within infected skin. The efficacies of the two tetramic acid analogues of the inventions at 10% were comparable to 2% mupirocin. This conclusion stems from statistical analysis of the resulting means by one way ANOVA followed by Tukey's test at $P<0.01$ with Placebo as the control group. Therefore, the tetramic acid analogues of the invention have the potential to be used clinically for the treatment of skin infections, such as those caused by *Staphylococcus aureus*. Together with the biofilm data described above in Example 10, the data indicates that the tetramic acid analogues of the invention may be used in treating biofilm associated skin disorders, such as persistent atopic dermatitis, impetigo or wound infections.

Further modifications, uses, and applications of the invention described herein will be apparent to those skilled in the art. It is intended that such modifications be encompassed in the following claims.

The invention claimed is:

1. A chemical compound selected from the group consisting of (S,Z)-1-benzyl-5-sec-butyl-3-(1-hydroxyethylidene)pyrrolidine-2,4-dione, (S,Z)-1-decyl-3-(1-hydroxyethylidene)-5-isobutylpyrrolidine-2,4-dione, (S,Z)-1,5-dibenzyl-3-(1-hydroxyethylidene)pyrrolidine-2,4-dione, (S,Z)-3-(1-hydroxyethylidene)-5-isobutyl-1-(3-methoxybenzyl)pyrrolidine-2,4-dione, (S,Z)-1-(4-fluorobenzyl)-3-(1-hydroxyethylidene)-5-isobutylpyrrolidine-2,4-dione, (R,Z)-1-(4-fluorobenzyl)-3-(1-hydroxyethylidene)-5-isobutylpyrrolidine-2,4-dione, (R,Z)-1,5-dibenzyl-3-(1-hydroxyethylidene)pyrrolidine-2,4-dione, (S,Z)-5-benzyl-1-ethyl-3-(1-hydroxyethylidene)pyrrolidine-2,4-dione, (S,Z)-1-decyl-3-(1-hydroxyethylidene)-5-isopropylpyrrolidine-2,4-dione, (S,Z)-1-butyl-3-(1-hydroxyethylidene)-5-isobutylpyrrolidine-2,4-dione, (S,Z)-1-(biphenyl-4-ylmethyl)-3-(1-hydroxyethylidene)-5-isobutylpyrrolidine-2,4-dione, (5S,Z)-1-((6,6-dimethylbicyclo[3.1.1]hept-2-en-2-yl)methyl)-3-(1-hydroxyethylidene)-5-isobutyl pyrrolidine-2,4-dione, (5S,Z)-1-(3,7-dimethyloct-6-enyl)-3-(1-hydroxyethylidene)-5-isobutylpyrrolidine-2,4-dione, (S,Z)-5-benzyl-1-decyl-3-(1-hydroxyethylidene)pyrrolidine-2,4-dione, and (R,Z)-1-decyl-3-(1-hydroxyethylidene)-5-isobutylpyrrolidine-2,4-dione.

2. The chemical compound of claim 1 which is (S,Z)-1-decyl-3-(1-hydroxyethylidene)-5-isobutylpyrrolidine-2,4-dione.

* * * * *